United States Patent
Fryfogle et al.

(10) Patent No.: US 10,172,781 B2
(45) Date of Patent: *Jan. 8, 2019

(54) PITUITOUS SILICONE FLUID

(71) Applicant: Dow Corning Corporation, Midland, MI (US)

(72) Inventors: Patrick J. Fryfogle, Midland, MI (US); Donald Anthony Kadlec, Midland, MI (US); Kimmai Thi Nguyen, Midland, MI (US); Ryan Christopher Thomas, Freeland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,335

(22) PCT Filed: Apr. 8, 2015

(86) PCT No.: PCT/US2015/024886
§ 371 (c)(1),
(2) Date: Jan. 18, 2017

(87) PCT Pub. No.: WO2016/014127
PCT Pub. Date: Jan. 28, 2016

(65) Prior Publication Data
US 2017/0165190 A1 Jun. 15, 2017
US 2017/0360690 A9 Dec. 21, 2017

Related U.S. Application Data

(60) Provisional application No. 62/028,002, filed on Jul. 23, 2014, provisional application No. 62/028,020, filed on Jul. 23, 2014.

(51) Int. Cl.
| | |
|---|---|
| A61K 8/06 | (2006.01) |
| C08K 5/56 | (2006.01) |
| A61K 8/895 | (2006.01) |
| A61Q 19/00 | (2006.01) |
| C08G 77/00 | (2006.01) |
| C08G 77/12 | (2006.01) |
| C08G 77/14 | (2006.01) |
| C08G 77/18 | (2006.01) |
| C08G 77/20 | (2006.01) |
| C08G 77/46 | (2006.01) |
| C08L 83/00 | (2006.01) |
| C08L 83/04 | (2006.01) |
| C08L 83/10 | (2006.01) |
| C08L 83/12 | (2006.01) |

(52) U.S. Cl.
CPC .............. *A61K 8/895* (2013.01); *A61K 8/062* (2013.01); *A61Q 19/00* (2013.01); *C08G 77/70* (2013.01); *C08K 5/56* (2013.01); *C08L 83/00* (2013.01); *C08L 83/04* (2013.01); *C08L 83/10* (2013.01); *C08L 83/12* (2013.01); *A61K 2800/54* (2013.01); *C08G 77/12* (2013.01); *C08G 77/14* (2013.01); *C08G 77/18* (2013.01); *C08G 77/20* (2013.01); *C08G 77/46* (2013.01)

(58) Field of Classification Search
CPC .... A61K 2800/54; A61K 8/062; A61K 8/895; A61Q 19/00; C08L 83/10; C08L 83/00; C08L 83/04; C08L 83/12; C08K 5/56; C08G 77/70; C08G 77/12; C08G 77/14; C08G 77/18; C08G 77/20; C08G 77/46
See application file for complete search history.

(56) References Cited

U.S. PATENT DOCUMENTS

| | | |
|---|---|---|
| 2,798,053 A | 7/1957 | Brown |
| 2,814,601 A | 11/1957 | Currie et al. |

(Continued)

FOREIGN PATENT DOCUMENTS

| | | |
|---|---|---|
| CA | 2510428 A1 | 7/2004 |
| EP | 0114607 A1 | 8/1984 |

(Continued)

OTHER PUBLICATIONS

English language abstract and machine translation for JP2005041795 (A) extracted from http://worldwide.espacenet.com database on Feb. 2, 2018, 12 pages.

(Continued)

*Primary Examiner* — Michael B. Pallay
(74) *Attorney, Agent, or Firm* — Warner Norcross & Judd LLP

(57) ABSTRACT

A pituitous silicone fluid includes a hydrosilylation reaction product and a carrier fluid. The hydrosilylation reaction product is the reaction product of a first linear organopolysiloxane and a second linear organopolysiloxane. The first linear organopolysiloxane includes ($R^1R^2R^3SiO_{1/2}$) and ($R^4R^5SiO_{2/2}$) units. Each of $R^1$-$R^5$ is independently a hydrocarbon group so long as at least one of R1-R5 is an alkenyl group. In addition, the first linear organopolysiloxane has a degree of polymerization of from 100 to 15,000. The second linear organopolysiloxane includes ($R^6R^7R^8SiO_{1/2}$) and ($R^9R^{10}SiO_{2/2}$) units. Each of $R^6$-$R^{10}$ is independently a hydrocarbon group, polyether group, siloxane group, or polyol group, so long as at least one of $R^6$-$R^{10}$ is a hydrogen atom. In addition, the second linear organopolysiloxane has a degree of polymerization of from 4 to 1,000. The hydrosilylation reaction product includes alkenyl or Si—H functionality. Personal care compositions can include the pituitous silicone fluid.

18 Claims, 13 Drawing Sheets

(56) References Cited

U.S. PATENT DOCUMENTS

| | | | |
|---|---|---|---|
| 2,857,356 | A | 10/1958 | Goodwin, Jr. |
| 3,159,601 | A | 12/1964 | Ashby |
| 3,220,972 | A | 11/1965 | Lamoreaux |
| 3,296,291 | A | 1/1967 | Chalk et al. |
| 3,419,593 | A | 12/1968 | Willing |
| 3,516,946 | A | 6/1970 | Modic |
| 3,715,334 | A | 2/1973 | Karstedt |
| 3,814,730 | A | 6/1974 | Karstedt |
| 3,923,705 | A | 12/1975 | Smith |
| 3,928,629 | A | 12/1975 | Chandra et al. |
| 3,958,581 | A | 5/1976 | Abegg et al. |
| 3,962,418 | A | 6/1976 | Birkofer |
| 3,989,668 | A | 11/1976 | Lee et al. |
| 4,009,256 | A | 2/1977 | Nowak, Jr. et al. |
| 4,122,029 | A | 10/1978 | Gee et al. |
| 4,165,336 | A | 8/1979 | Bouillon et al. |
| 4,250,108 | A | 2/1981 | Bouillon et al. |
| 4,290,974 | A | 9/1981 | Bouillon et al. |
| 4,387,089 | A | 6/1983 | De Polo |
| 4,489,057 | A | 12/1984 | Welters et al. |
| 4,562,067 | A | 12/1985 | Hopp et al. |
| 4,585,597 | A | 4/1986 | Lang et al. |
| 4,704,272 | A | 11/1987 | Oh et al. |
| 4,741,855 | A | 5/1988 | Grote et al. |
| 4,775,526 | A | 10/1988 | Lang et al. |
| 4,788,006 | A | 11/1988 | Bolich, Jr. et al. |
| 5,036,117 | A | 7/1991 | Chung et al. |
| 5,175,325 | A | 12/1992 | Brown et al. |
| 5,236,986 | A * | 8/1993 | Sakuta .................. A61K 8/894 524/267 |
| 5,387,417 | A | 2/1995 | Rentsch |
| 5,643,557 | A | 7/1997 | Eteve et al. |
| 5,695,747 | A | 12/1997 | Forestier et al. |
| 5,762,912 | A | 6/1998 | Eteve |
| 5,811,487 | A | 9/1998 | Schulz, Jr. et al. |
| 5,919,441 | A | 7/1999 | Mendolia et al. |
| 5,981,680 | A | 11/1999 | Petroff et al. |
| 6,013,682 | A | 1/2000 | Dalle et al. |
| 6,051,216 | A | 4/2000 | Barr et al. |
| 6,075,087 | A | 6/2000 | Juen et al. |
| 6,200,581 | B1 | 3/2001 | Lin et al. |
| 6,306,992 | B1 | 10/2001 | Yoshitake et al. |
| 6,420,504 | B1 | 7/2002 | Yoshitake et al. |
| 6,605,734 | B2 | 8/2003 | Roy et al. |
| 6,987,157 | B2 | 1/2006 | Clement et al. |
| 7,078,026 | B2 | 7/2006 | Ferrari et al. |
| 7,452,849 | B2 | 11/2008 | Berry et al. |
| 7,803,358 | B2 | 9/2010 | Gordan et al. |
| 8,012,544 | B2 | 9/2011 | Liu |
| 8,017,712 | B2 | 9/2011 | Berry et al. |
| 2003/0072730 | A1 | 4/2003 | Toumilhac |
| 2003/0170188 | A1 | 9/2003 | Ferrari et al. |
| 2003/0235553 | A1 | 12/2003 | Lu et al. |
| 2004/0138376 | A1 | 7/2004 | Awad |
| 2004/0180032 | A1 | 9/2004 | Manelski et al. |
| 2010/0247460 | A1 | 9/2010 | Lin et al. |
| 2010/0303743 | A1 | 12/2010 | Kennan et al. |
| 2012/0220549 | A1 | 8/2012 | Starch et al. |
| 2012/0251598 | A1 | 10/2012 | Ikeda et al. |
| 2014/0249106 | A1 | 9/2014 | Starch et al. |

FOREIGN PATENT DOCUMENTS

| | | |
|---|---|---|
| EP | 0487404 A1 | 5/1992 |
| EP | 0501791 A2 | 9/1992 |
| EP | 0518772 A1 | 12/1992 |
| EP | 0518773 A1 | 12/1992 |
| EP | 0678292 A1 | 10/1995 |
| EP | 1266647 A1 | 12/2002 |
| EP | 1266648 A1 | 12/2002 |
| EP | 1266653 A1 | 12/2002 |
| EP | 2505612 A1 | 10/2012 |
| FR | 2236515 A1 | 2/1975 |
| FR | 2282426 A2 | 3/1976 |
| FR | 2326405 A1 | 4/1977 |
| FR | 2430938 A1 | 2/1980 |
| FR | 2440933 A1 | 6/1980 |
| FR | 2592380 A1 | 7/1987 |
| FR | 2645148 A1 | 10/1990 |
| GB | 2423250 A | 8/2006 |
| JP | H04272932 A | 9/1992 |
| JP | 2005041795 A | 2/2005 |
| JP | 2005314369 A | 11/2005 |
| JP | 2010540550 A | 12/2010 |
| JP | 2013503940 A | 2/2013 |
| KR | 1020100061699 A | 6/2010 |
| WO | WO9522311 A1 | 8/1995 |
| WO | WO03101412 A2 | 12/2003 |
| WO | WO03105789 A1 | 12/2003 |
| WO | WO03105801 A1 | 12/2003 |
| WO | WO03106614 A2 | 12/2003 |
| WO | WO2004000247 A1 | 12/2003 |
| WO | WO2004052982 A2 | 6/2004 |
| WO | WO2004054523 A1 | 7/2004 |
| WO | WO2004054524 A1 | 7/2004 |
| WO | WO2004060101 A2 | 7/2004 |
| WO | WO2004060271 A2 | 7/2004 |
| WO | WO2004060276 A2 | 7/2004 |
| WO | WO2009090074 A1 | 7/2009 |
| WO | WO2010065712 A1 | 6/2010 |
| WO | WO2013117490 A1 | 8/2013 |
| WO | WO2014019841 A1 | 2/2014 |
| WO | WO2016014127 A1 | 1/2016 |
| WO | WO2016014128 A1 | 1/2016 |

OTHER PUBLICATIONS

English language abstract and machine translation for JP2005314369 (A) extracted from http://worldwide.espacenet.com database on Feb. 2, 2018, 23 pages.

PCT/US2015/024905 International Search Report dated Jun. 24, 2015, 4 pages.

English language abstract and machine translation for FR2282426 (A2) extracted from http://worldwide.espacenet.com database on Oct. 28, 2016, 15 pages.

English language abstract and machine translation for FR2645148 (A1) extracted from http://worldwide.espacenet.com database on Oct. 24, 2016, 31 pages.

PCT/US2015/024886 International Search Report dated Jun. 30, 2015, 4 pages.

* cited by examiner

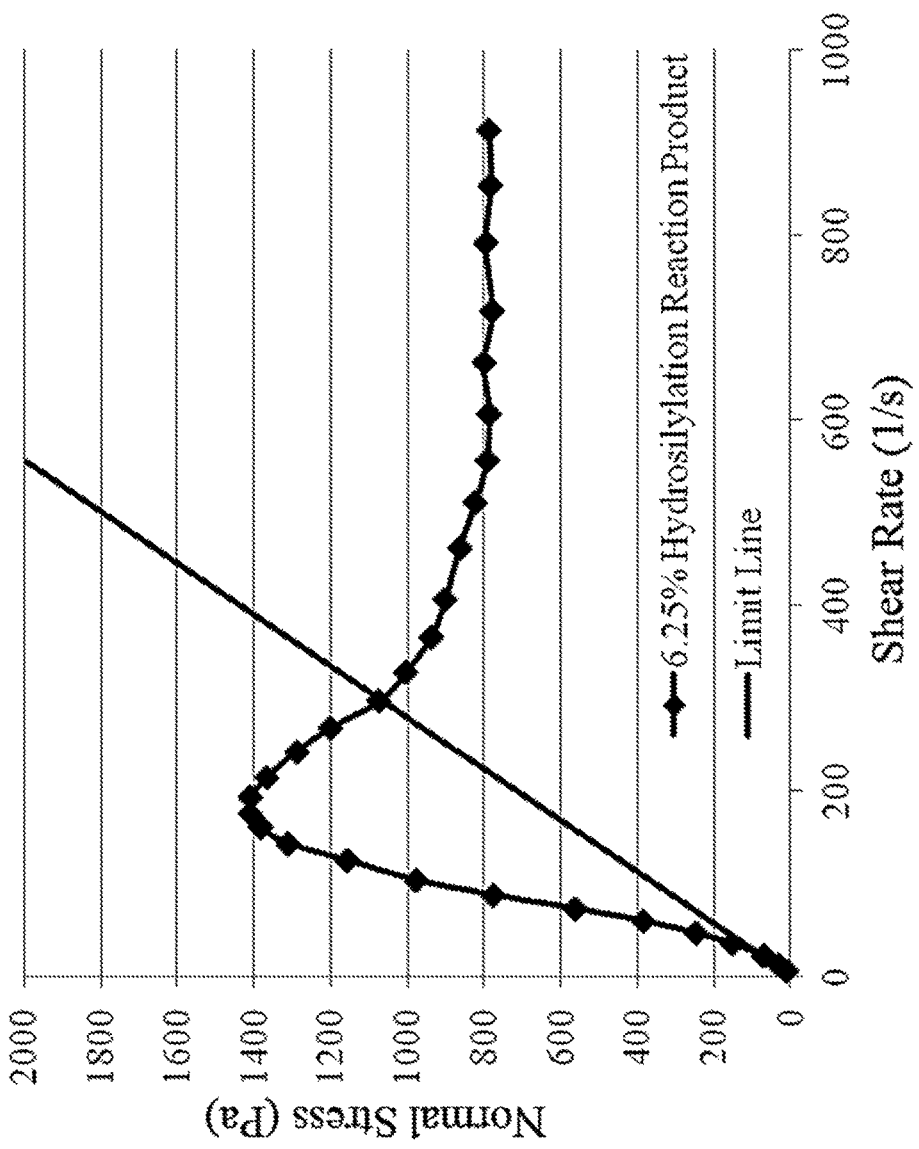

PITUITOUS SILICONE FLUID

CROSS-REFERENCE TO RELATED APPLICATIONS

This application is the National Stage of International Application No. PCT/US2015/024886 filed on 8 Apr. 2015, which claims priority to and all advantages of U.S. Provisional Patent Application Nos. 62/028,002 and 62/028,020, each filed on Jul. 23, 2014, the content of which is hereby incorporated by reference.

FIELD OF THE INVENTION

This disclosure generally relates to a pituitous silicone fluid. More specifically, this disclosure generally relates to a pituitous silicone fluid including a carrier fluid and a hydrosilylation reaction product of two linear organopolysiloxanes.

BACKGROUND OF THE INVENTION

Silicone fluids are widely used in industry. The most common silicone fluids used are dimethylsiloxane fluids, which are typically low molecular weight cyclic molecules. However, high molecular weight and highly branched fluids are also used in many applications.

The phenomenon of a viscoelastic liquid climbing a rotating rod, known as the Weissenberg effect, has been observed in polymer solutions, and in pituitous silicone fluids as described by Starch et al. (US Pub. No. 2012/0220549 A1). This behavior is representative of entanglements between polymer chains that develop under shear stress. These pituitous silicone fluids are high molecular weight, highly branched organopolysiloxanes that are used in personal care products and are shown, for example, in FIGS. 1A and 1B.

These branched organopolysiloxanes are obtainable by the reaction of organohydrogencyclosiloxanes with alkenyl functionalized polydimethylsiloxanes. However, these pituitous silicone fluids are formed using a process that is very sensitive to stoichiometry. For this reason, it is difficult to produce consistently high yields of predictable products. Moreover, these highly branched organopolysiloxanes are sterically hindered such that large side chains are difficult to add. Therefore, there remains an opportunity for improvement.

BRIEF DESCRIPTION OF THE DRAWINGS

Other advantages of the present disclosure will be readily appreciated, as the same becomes better understood by reference to the following detailed description when considered in connection with the accompanying drawings wherein:

FIG. 11 is a line graph of stress as a function of shear of the pituitous silicone fluid of Example 7.

BRIEF SUMMARY OF THE INVENTION

Figure 1A:
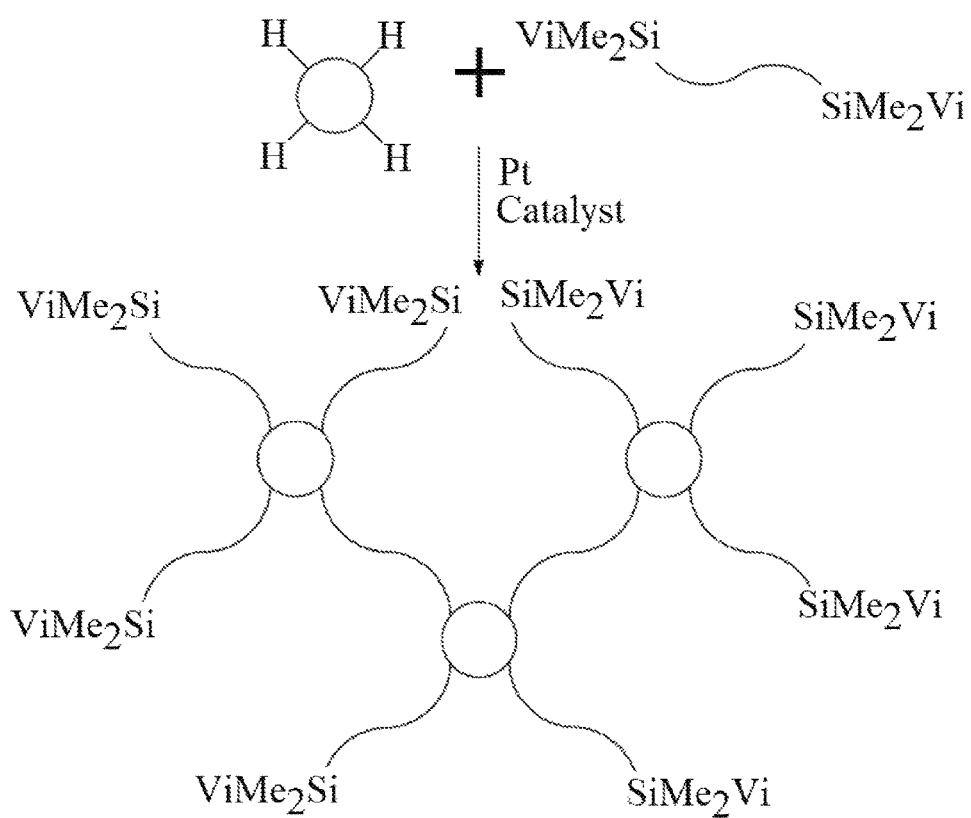
FIG. 1A is a general reaction schematic showing a reaction of the prior art utilizing highly branched/cyclic reactants.
Figure 1B:
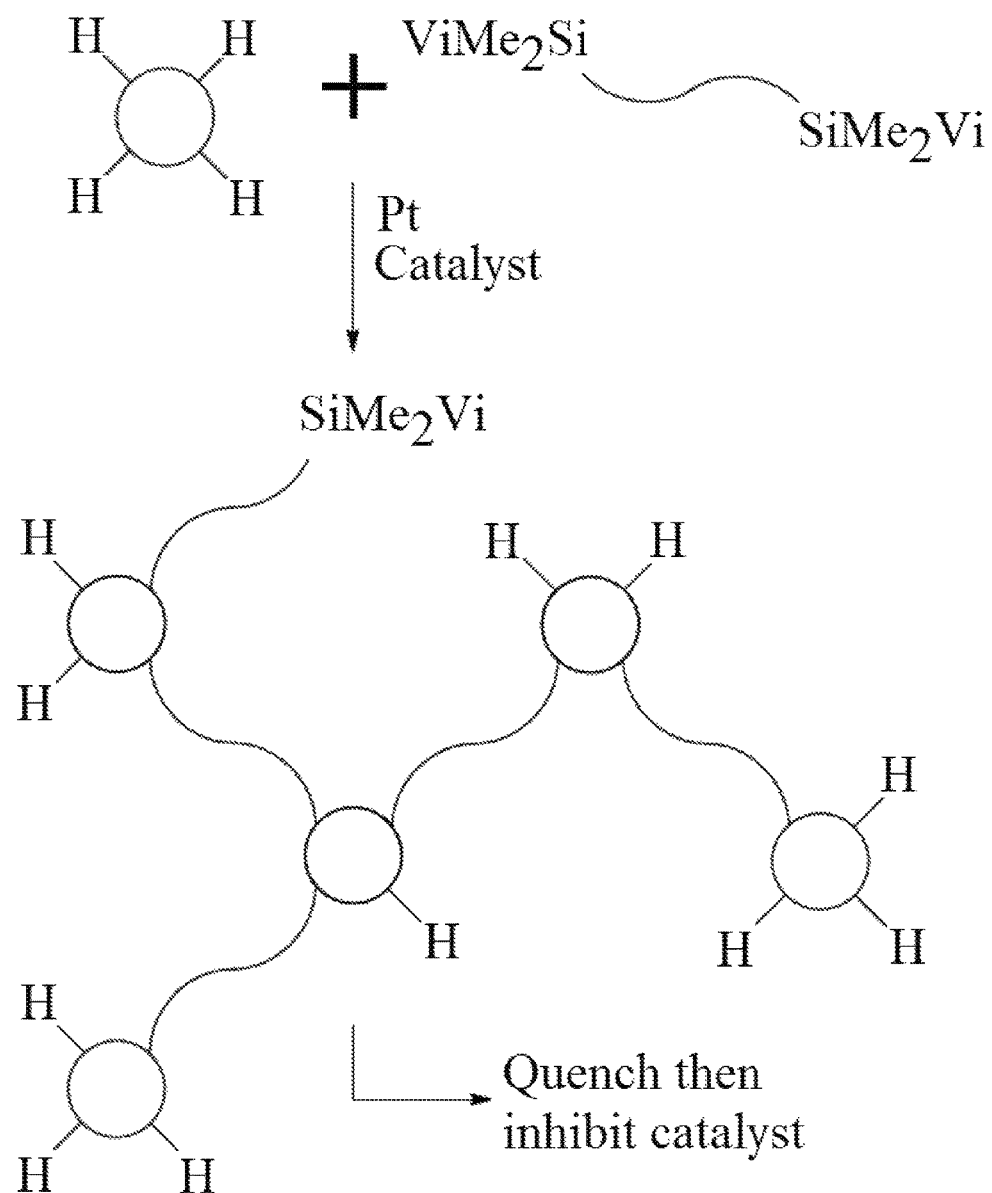
FIG. 1B is a second general reaction schematic showing a reaction of the prior art utilizing highly branched/cyclic reactants.

This disclosure provides a pituitous silicone fluid. The pituitous silicone fluid includes a hydrosilylation product and a carrier fluid. The carrier fluid is chosen from a silicone fluid, an organic solvent, an organic oil, and combinations thereof. The hydrosilylation reaction product is the reaction product of a first linear organopolysiloxane and a second linear organopolysiloxane. The first linear organopolysiloxane includes $(R^1R^2R^3SiO_{1/2})$ and $(R^4R^5SiO_{2/2})$ units. Each of $R^1$-$R^5$ is independently a hydrocarbon group so long as at least one of $R^1$-$R^5$ is an alkenyl group. In addition, the first linear organopolysiloxane includes less than 1 weight percent of T and Q units and has a degree of polymerization of from 100 to 15,000. The second linear organopolysiloxane includes $(R^6R^7R^8SiO_{1/2})$ and $(R^9R^{10}SiO_{2/2})$ units. Each of $R^6$-$R^{10}$ is independently a hydrocarbon group so long as at least one of $R^6$-$R^{10}$ is a hydrogen atom. The second linear organopolysiloxane includes less than 1 weight percent of T and Q units and has a degree of polymerization of from 4 to 1,000. The hydrosilylation reaction product also includes alkenyl or Si—H functionality. Moreover, the hydrosilylation reaction product is present in an amount of from 3 to 30 parts by weight per 100 parts by weight of the pituitous silicone fluid. Furthermore, the pituitous silicone fluid exhibits an increasing normal stress observed in a perpendicular direction when a constantly increasing shear force is applied.

The pituitous silicone fluid of this disclosure is typically formed using a method that is highly repeatable and is not highly sensitive to stoichiometry of reactants. This allows for consistency in both formation and yield of the pituitous silicone fluid. Moreover, the linear nature of the first and second organopolysiloxanes reduces steric hindrance during reaction, thereby allowing large side chains to be more easily added to the hydrosilylation reaction product. In addition, the first and second organopolysiloxanes are easy to obtain and react.

Furthermore, the pituitous silicone fluid can form a pseudo-film on skin when utilized in a personal care composition. This provides improved coverage on skin and longer lasting physical properties.

DETAILED DESCRIPTION

This disclosure provides a pituitous silicone fluid, i.e., a silicone fluid that exhibits pituitous properties. As used herein, "pituitous" describes a rheological property of the silicone fluid wherein the fluid exhibits an increasing normal stress observed in a perpendicular direction when a constantly increasing shear force is applied. For example, when the pituitous silicone fluid is subjected to shear stress in the x-y plane, a force is developed in the z direction (perpendicular or normal to the plane of shear). Pituitous rheology of the silicone fluid may be measured using a controlled stress rheometer. Such rheometers are commercially available, such as TA Instruments AR 1000-N (109 Lukens Drive, New Castle Del. 19720). Typically, a fluid sample is held between a flat disc (attached to the rheometer) and a stationary plate equipped with a load cell. A controlled amount of force (torque) is applied to the shaft attached to the disc thus subjecting the sample to a shear stress. The torque is increased and the disc rotates at an increasing rate, which is recorded as the shear rate. As the sample is being subjected to the shear stress, the normal stress is recorded by the load cell. The results of the evaluations of the rheological properties are generally reported as a plot of normal stress (in Pascals) vs. a perpendicular shear rate (in $\sec^{-1}$). In other embodiments, a fluid is considered pituitous if a plot of normal stress versus shear rate falls above a limit line on a graph wherein the limit line is created using the equation $y=3.6x$, where y in the normal stress and x is the shear rate. However, the results are not limited to such types of reporting and may be reported or evaluated using any technique appreciated in the art.

Hydrosilylation Reaction Product:

The hydrosilylation reaction product is the reaction product of a first linear organopolysiloxane and a second linear organopolysiloxane. Said differently, the hydrosilylation reaction product is formed from the hydrosilylation reaction of the first and second linear organopolysiloxanes. Typically, the hydrosilylation reaction product is itself linear. In various embodiments, the terminology linear describes that the first linear organopolysiloxane, second linear organopolysiloxane, hydrosilylation reaction product, and/or pituitous silicone fluid itself include <1, <0.5, <0.1, or <0.01, weight percent of T and Q units, i.e., siloxy units having the formulae (substituent-$SiO_{3/2}$) and ($SiO_{4/2}$), respectively. In other embodiments, the terminology "linear" describes that the first linear organopolysiloxane, second linear organopolysiloxane, hydrosilylation reaction product, and/or pituitous silicone fluid itself, is not branched or is not highly branched. In still other embodiments, the backbone of the first linear organopolysiloxane, second linear organopolysiloxane, hydrosilylation reaction product, and/or pituitous silicone fluid itself is described as being linear, e.g. not branched or highly branched. For example, while the backbone of the first linear organopolysiloxane, second linear organopolysiloxane, hydrosilylation reaction product, and/or pituitous silicone fluid itself is typically linear, the backbone may have one or more cyclic, aromatic, or otherwise non-linear substituents attached thereto. In such a scenario, the backbone of, and the first linear organopolysiloxane, second linear organopolysiloxane, hydrosilylation reaction product, and/or pituitous silicone fluid themselves, would still be considered "linear" as used herein. Moreover, the terms "branched" and "highly branched" used above are used as understood by those of skill in the art.

One or more than one first linear organopolysiloxane can be reacted with one or more than one second linear organopolysiloxane. Similarly, in various embodiments, one first linear organopolysiloxane is reacted with two (or more) second linear organopolysiloxanes. Alternatively, two (or more) first linear organopolysiloxanes may be reacted with one second linear organopolysiloxane. Thus, in various embodiments, wherever "first linear organopolysiloxane" is used herein, two or more first linear organopolysiloxanes can be used. In other embodiments, wherever "second linear organopolysiloxane" is used herein, two or more second linear organopolysiloxanes can be used.

Figure 2:
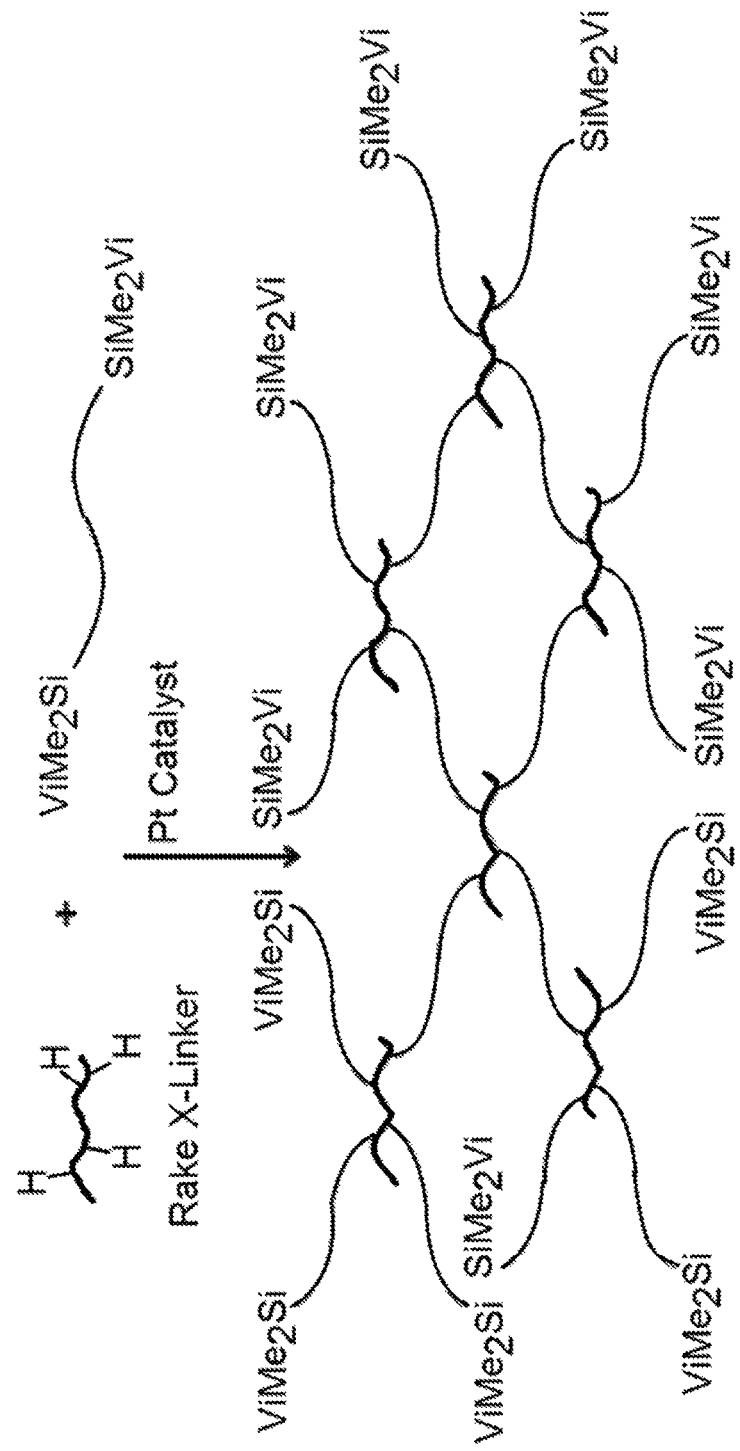
FIG. 2 is a general reaction schematic showing one non-limiting reaction of this disclosure utilizing a first linear organopolysiloxane and a second linear organopolysiloxane.
Figure 3:
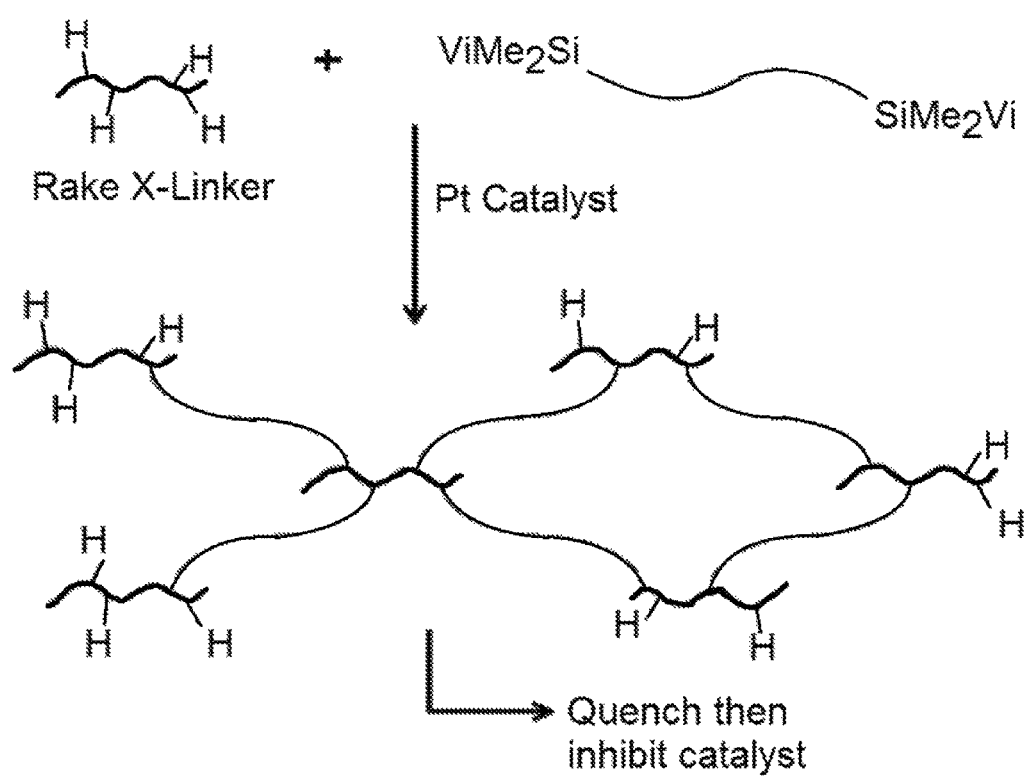
FIG. 3 is a general reaction schematic showing a second non-limiting reaction of this disclosure utilizing a first linear organopolysiloxane and a second linear organopolysiloxane.
Figure 4:
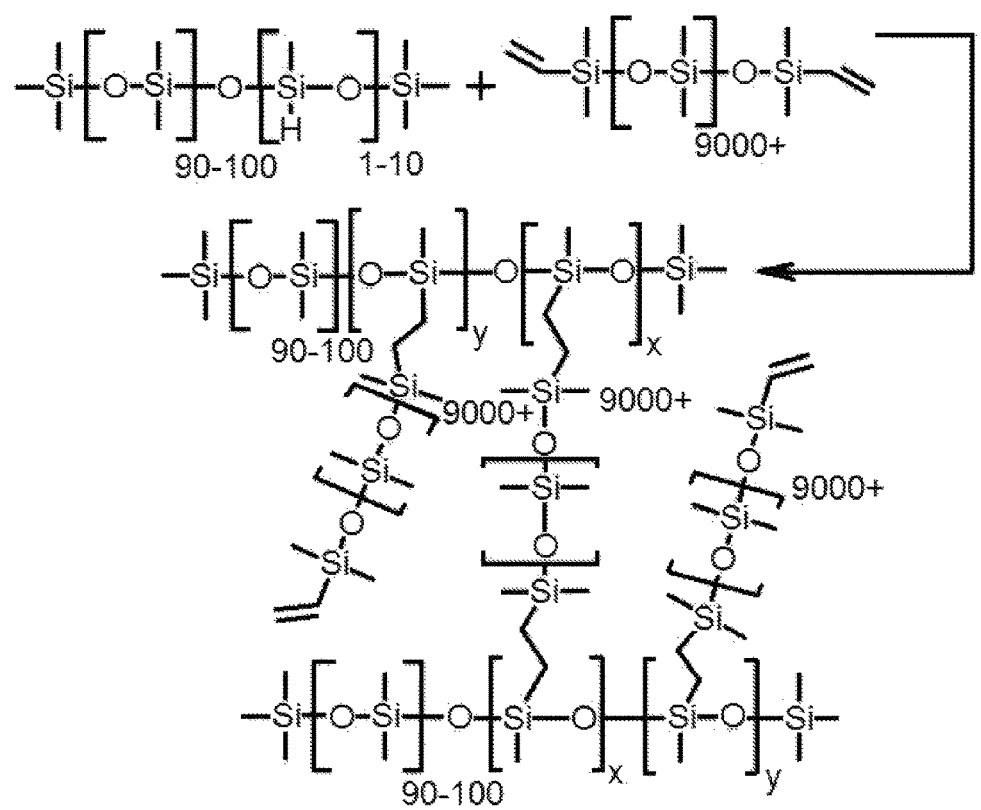
FIG. 4 is a general reaction schematic showing a third non-limiting reaction of this disclosure utilizing a first linear organopolysiloxane and a second linear organopolysiloxane.

The hydrosilylation reaction product includes alkenyl or Si—H functionality (e.g. as the result of the reaction of the first and second linear organopolysiloxanes). In various embodiments, the alkenyl or Si—H functionality may be observed on a parts per million (ppm) or parts per billion (ppb) level, based on a total weight of the hydrosilylation reaction product and/or pituitous silicone fluid. In other embodiments, the alkenyl or Si—H functionality is understood based on a molar ratio of alkenyl to Si—H functionality of the reactants (e.g. the first and second linear organopolysiloxanes) used to form the hydrosilylation reaction product. For example, the ratio of alkenyl to Si—H units used to form the hydrosilylation reaction product (e.g. from the first and second linear organopolysiloxanes) may be <1 or >1. In various embodiments, this ratio is from 0.01 to <1, 0.1 to <1, 0.2-0.9, 0.3-0.8, 0.4-0.7, or 0.5-0.6. In other embodiments, this ratio is >1, from >1 to 100, >1 to 50, >1 to 25, >1 to 15, >1 to 10, or >1 to 5. Typically, the ratio of alkenyl to Si—H units is not exactly 1. However, a ratio of 1 is contemplated in one embodiment. It is contemplated that any and all values or ranges of values between those described above may also be utilized. FIGS. 2, 3 and 4 generally show hydrosilylation reaction products having alkenyl functionality.

In various embodiments, the hydrosilylation reaction product is present in an amount of from 3-30, 3-25, 4-25, 5-25, 5-20, 5-15, 5-10, 5-9, 6-9, or 7-8, parts by weight per 100 parts by weight of the pituitous silicone fluid. This amount, in parts by weight, may also be described as a "percent solids" or "percent active(s)." It is contemplated that any and all values or ranges of values between those described above may also be utilized.

The hydrosilylation reaction product may be described as an elastomer, e.g. a loosely cross-linked elastomer. When combined with the carrier fluid, the hydrosilylation reaction product is fairly soluble therein. The degree of polymerization of the hydrosilylation reaction product itself can depend on the degrees of polymerization of the first and second linear organopolysiloxanes. In various embodiments, a high degree of polymerization of both the first and second linear organopolysiloxanes imparts tight cross-linking to the hydrosilylation reaction product. In other embodiments, a high degree of polymerization of one or the other of the first and second linear organopolysiloxanes imparts a medium degree of cross-linking to the hydrosilylation reaction product. In still other embodiments, a low degree of polymerization of both the first and second linear organopolysiloxanes imparts a low, e.g. loose, degree of cross-linking to the hydrosilylation reaction product.

First Linear Organopolysiloxane:

The first linear organopolysiloxane includes ($R^1R^2R^3SiO_{1/2}$) and ($R^4R^5SiO_{2/2}$) units, also known as M and D units, respectively. Each of $R^1$-$R^5$ is independently a hydrocarbon group so long as at least one of $R^1$-$R^5$ is an alkenyl group. The hydrocarbon group may be an alkyl group having 1-20, 2-15, 3-10, 5-10, etc., carbon atoms, such as methyl, ethyl, propyl, butyl, pentyl and hexyl; cycloalkyl groups, such as cyclohexyl and cycloheptyl; aryl groups having 6-12 carbon atoms, such as phenyl, tolyl and xylyl; or aralkyl groups having 7-20 carbon atoms, such as benzyl and phenylethyl. The hydrocarbon group may also be an alkenyl group having 2-20 carbon atoms, such as vinyl, allyl, butenyl, pentenyl, hexenyl and decenyl, typically vinyl or hexenyl groups. Alternatively, the hydrocarbon group may include one or more halogen atoms. It is contemplated that any and all values or ranges of values between those described above may also be utilized.

The first linear organopolysiloxane can be a homopolymer, a copolymer or a terpolymer. Non-limiting examples include copolymers including dimethylsiloxy units and phenylmethylsiloxy units, copolymers including dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others. The first linear organopolysiloxane typically has a linear backbone but may include non-linear substituents attached to the backbone.

In various embodiments, the first linear organopolysiloxane includes <1, <0.5, <0.1, or <0.01, weight percent of T and/or Q units. Alternatively, the first linear organopolysiloxane is free of T and/or Q units. In other embodiments, the first linear organopolysiloxane has a degree of polymerization (DP) of from 100-15,000, 500-15,000, 2,000-15,000, 5,000-15,000, 7,500-15,000, 8,000-15,000, 10,000-12,000, or about 10,000. It is contemplated that any and all values or ranges of values between those described above may also be utilized.

In one embodiment, the first linear organopolysiloxane is a polydiorganosiloxane gum. As used herein, polydiorganosiloxane gums include predominately D units. For example, the polydiorganosiloxane gum may itself have a viscosity of at least 1,000,000, or at least 2,000,000, mm$^2$/s at 25° C. Alternatively, the molecular weight may be sufficient to impart a Williams plasticity number of at least 40 as determined by the American Society for Testing and Materials (ASTM) test method 926 to the polydiorganosiloxane gum. Typically, the plasticity number is 40-200 or 50-150. Alternatively, the molecular weight of the polydiorganosiloxane gum is at least 600,000, at least 1,000,000, or at least 2,000,000, Daltons. It is contemplated that any and all values or ranges of values between those described above may also be utilized.

Specific non-limiting illustrations of polydiorganosiloxane gums include: trimethylsiloxy-endblocked dimethylsiloxane, trimethylsiloxy-endblocked dimethylsiloxane-methylvinylsiloxane copolymers; trimethylsiloxy-endblocked methylphenylsiloxane-dimethylsiloxane-methylvinylsiloxane copolymers; trimethylsiloxy-endblocked 3,3,3-trifluoropropylmethyl siloxane copolymers; trimethylsiloxy-endblocked 3,3,3-trifluoropropylmethyl-methylvinylsiloxane copolymers; dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers; and similar copolymers wherein at least one end group is dimethylhydroxysiloxy. The polydiorganosiloxane gum may also be or include a combination of two or more organopolysiloxanes. Methods for preparing polydiorganosiloxane gums are well known and many are commercially available.

In other embodiments, the first linear organopolysiloxane is a fluid. For example, the fluid may have a viscosity of from 1,000-100,000, 25,000-100,000, 25,000-75,000, 50,000-75,000, 50,000-65,000, or 55,000-60,000, mm$^2$/s at 25° C. The fluid may alternatively have a molecular weight of from 7,500-700,000, 50,000-500,000, or 100,000-250,000, Daltons. In other embodiments, DOW CORNING® ("DC") fluids; 4-2764, 2-7891, 2-7754, 2-7891, and 2-7463, SFD-117, SFD-119, SFD-120, SFD-128, SFD-129, 5-8709, LV, 2-7038, 2-7892, 2-7287, 2-7463, dihexenyl terminal 7692, 7697, along with 2-7063 and 2-7748, and combinations thereof, can be used. It is contemplated that any and all values or ranges of values between those described above may also be utilized.

Second Linear Organopolysiloxane:

The second linear organopolysiloxane includes $(R^6R^7R^8SiO_{1/2})$ and $(R^9R^{10}SiO_{2/2})$ units. Each of $R^6$-$R^{10}$ is independently a hydrocarbon group so long as at least one of $R^6$-$R^{10}$ is a hydrogen atom. The hydrocarbon group may be any described above.

In various embodiments, the second linear organopolysiloxane includes <1, <0.5, <0.1, or <0.01, weight percent of T and/or Q units. Alternatively, the second linear organopolysiloxane may be entirely free of T and/or Q units. In other embodiments, the second linear organopolysiloxane has a degree of polymerization of from 4-1,000, 8-500, 25-400, 50-300, 75-200, or 75-100, alternatively 100-500, 100-400, 100-300, 100-200, 75-150, 75-125, or about 100. It is contemplated that any and all values or ranges of values between those described above may also be utilized.

The second linear organopolysiloxane may be a gum or a fluid, as described above. Non-limiting examples of the second linear organopolysiloxane are DC fluids; 5-0210, 6-3570, 1-8114, 1-3502, OFX-5057, OFX-5084, OFX-5625, MHX-1107, and combinations thereof. These are all commercially available products that represent SiH pendant, SiH terminal, or SiH homopolymers.

The first and second linear organopolysiloxanes typically react together to form the hydrosilylation product. This reaction typically takes place in the presence of a hydrosilylation catalyst. The hydrosilylation catalyst may be any known in the art. For example, the hydrosilylation catalyst may be a platinum group metal-containing catalyst. By "platinum group" it is meant ruthenium, rhodium, palladium, osmium, iridium and platinum and complexes thereof. Non-limiting examples of platinum group metal-containing catalysts useful herein are the platinum complexes prepared as described in U.S. Pat. Nos. 3,419,593; 5,175,325; 3,989,668; 5,036,117; 3,159,601; 3,220,972; 3,296,291; 3,516,946; 3,814,730; and 3,928,629; each of which is expressly incorporated herein by reference in one or more non-limiting embodiments. The platinum-containing catalyst can be platinum metal, platinum metal deposited on a carrier, such as silica gel or powdered charcoal, or a compound or complex of a platinum group metal. Typical platinum-containing catalysts include chloroplatinic acid, either in hexahydrate form or anhydrous form, and/or a platinum-containing catalyst which is obtained by a method comprising reacting chloroplatinic acid with an aliphatically unsaturated organosilicon compound, such as divinyltetramethyldisiloxane, or alkene-platinum-silyl complexes as described in U.S. Pat. No. 6,605,734, which is expressly incorporated herein by reference in one or more non-limiting embodiments. An example is $(COD)Pt(SiMeCl_2)_2$, where "COD" is 1,5-cyclooctadiene and "Me" is methyl. These alkene-platinum-silyl complexes may be prepared, e.g., by mixing 0.015 mole $(COD)PtCl_2$ with 0.045 mole COD and 0.0612 moles HMeSiCl$_2$.

The amount of hydrosilylation catalyst used typically depends upon the particular catalyst. The hydrosilylation catalyst is typically utilized in an amount sufficient to provide at least 2 ppm, more typically 4-200 ppm of platinum based on total weight percent solids (all non-solvent ingredients), based on one million parts of the pituitous silicone fluid. In various embodiments, the hydrosilylation catalyst is present in an amount sufficient to provide 1-150 weight ppm of platinum on the same basis. The hydrosilylation catalyst may be added as a single species or as a mixture of two or more different species.

Optional Compound(s):

The pituitous silicone fluid may also include one or more optional compounds. Alternatively, the hydrosilylation reaction product may be further defined as the reaction product of the first linear organopolysiloxane, second linear organopolysiloxane, and one or more of the following optional compounds, e.g. in the presence of the aforementioned hydrosilylation catalyst. Alternatively, the first linear organopolysiloxane may be reacted with the optional compound before reaction with the second linear organopolysiloxane. In other embodiments, the second linear organopolysiloxane may be reacted with the optional compound before reaction with the first linear organopolysiloxane and still fall within the general description of the second linear organopolysiloxane. For example, in one embodiment, a first type of second linear organopolysiloxane may be reacted with the optional compound to form a second type of second linear organopolysiloxane. Alternatively, this first type of second linear organopolysiloxane may be described as a (first) species of the broad second linear organopolysiloxane. In one embodiment, the second linear organopolysiloxane includes the reaction product of a first species of the second linear organopolysiloxane and a compound having a mono terminal aliphatic unsaturated hydrocarbon group or any other optional compound described herein.

Non-limiting examples of such optional compounds include a compound or mixture of compounds having a mono terminal aliphatic unsaturated hydrocarbon group. For example, this optional compound may be or include a hydrocarbon containing 6-30 carbon atoms having one terminal unsaturated aliphatic hydrocarbon group, and/or a polyoxyalkylene having one terminal unsaturated aliphatic group.

Use of this optional compound can alter the resulting chemical and physical properties of the hydrosilylation reaction product and/or pituitous silicone fluid. For example, the optional compound may add hydrocarbon groups to the hydrosilylation reaction product, thus adding more hydrophobic character to the pituitous silicone fluid. Conversely, if the optional compound is, e.g. a polyoxyalkylene having a majority of ethylene oxide units, use may result in increased hydrophilicity of the hydrosilylation reaction product and/or pituitous silicone fluid.

The unsaturated aliphatic hydrocarbon group(s) in the optional compound can be an alkenyl or alkynyl group. Representative, non-limiting examples of alkenyl groups are shown by the following structures; $H_2C=CH-$, $H_2C=CHCH_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures; $HC≡C-$, $HC≡CCH_2-$, $HC≡CC(CH_3)-$, $HC≡CC(CH_3)_2-$, and $HC≡CC(CH_3)_2CH_2-$.

In other embodiments, the hydrocarbon containing 6-30 carbons having one terminal unsaturated aliphatic group may be selected from α-olefins, such as 1-hexene, 1-octene, 1-decene, 1-undecene, 1-decadecene, and similar homologs. Alternatively, the optional compound may also be selected from aryl containing hydrocarbons, such as α-methyl styrene.

Still further, the optional compound may be selected from those polyoxyalkylenes having the average formula: R'O—$[(C_2H_4O)_{c'}(C_3H_6O)_{d'}(C_4H_8O)_{e'}]$—R" where R' is a monovalent unsaturated aliphatic hydrocarbon group containing 2-12 carbon atoms, c' is from 0-100, d' is from 0-100, and "e" is from 0-100, provided the sum of c', d', and e is >0. R" is hydrogen, an acyl group, or a monovalent hydrocarbon group containing 1-8 carbons. Representative, non-limiting examples of polyoxyalkylenes, useful as the optional compound include; $H_2C=CHCH_2O(C_2H_4O)_{c'}H$; $H_2C=CHCH_2O(C_2H_4O)_{c'}CH_3$; $H_2C=CHCH_2O(C_2H_4O)_{c'}C(O)CH_3$; $H_2C=CHCH_2O(C_2H_4O)_{c'}(C_3H_6O)_{d'}H$; $H_2C=CHCH_2O(C_2H_4O)_{c'}(C_3H_6O)_{d'}CH_3$; $H_2C=C(CH_3)CH_2O(C_2H_4O)_{c'}H$; $H_2C=CC(CH_3)_2O(C_2H_4O)_{c'}H$; $H_2C=C(CH_3)CH_2O(C_2H_4O)_{c'}CH_3$; $H_2C=C(CH_3)CH_2O(C_2H_4O)_{c'}C(O)CH_3$; $H_2C=C(CH_3)CH_2O(C_2H_4O)_{c'}(C_3H_6O)_{d'}H$; $H_2C=C(CH_3)CH_2O(C_2H_4O)_{c'}(C_3H_6O)_{d'}CH_3$; $HC≡CCH_2O(C_2H_4O)_{c'}{}^1H$; $HC≡CCH_2O(C_2H_4O)_{c'}CH_3$; $HC≡CCH_2O(C_2H_4O)_{c'}(C_3H_6O)_{d'}H$; $HC≡CCH_2O(C_2H_4O)_{c'}(C_3H_6O)_{d'}CH_3$; and $HC≡CCH_2O(C_2H_4O)_{c'}C(O)CH_3$; wherein c' and d' are as described above.

In still other embodiments, the optional compound is a linear or branched siloxane with one unsaturated aliphatic group. Alternatively, the optional compound may be a polyol having one unsaturated aliphatic group (e.g. allyl xylitol or allyl glycerin).

Carrier Fluid:

The pituitous silicone fluid also includes a carrier fluid. The carrier fluid is typically chosen from a silicone fluid, an organic solvent, an organic oil, and combinations thereof. Suitable carrier fluids include silicones, both linear and cyclic, organic oils, organic solvents and combinations of these. Specific examples of solvents may be found in U.S. Pat. No. 6,200,581, which is hereby expressly incorporated by reference in various non-limiting embodiments relative to these solvents. In one embodiment, the carrier fluid is a polydimethylsiloxane. In various other embodiments, the carrier fluid is a low viscosity silicone or a volatile methyl siloxane or a volatile ethyl siloxane or a volatile methyl ethyl siloxane having a viscosity from 1-1,000 mm²/s measured at 25° C., such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadecamethylheptasiloxane, heptamethyl-3-{(trimethylsilyl)oxy)}trisiloxane, hexamethyl-3,3,bis{(trimethylsilyl)oxy}trisiloxane, and pentamethyl{(trimethylsilyl)oxy}cyclotrisiloxane, as well as polydimethylsiloxanes, polyethylsiloxanes, polymethylethylsiloxanes, polymethylphenylsiloxanes, polydiphenylsiloxanes, and combinations thereof. Examples of suitable carrier fluids include DOW CORNING® 200 Fluids, e.g. 2 cSt and 5 cSt; and DOW CORNING® FZ-3196.

The organic solvent may include, but is not limited to, aromatic hydrocarbons, aliphatic hydrocarbons, alcohols, aldehydes, ketones, amines, esters, ethers, glycols, glycol ethers, alkyl halides, aromatic halides, and combinations thereof. Hydrocarbons including isododecane, isohexadecane, Isopar L ($C_{11}$-$C_{13}$), Isopar H ($C_{11}$-$C_{12}$), hydrogentated polydecene, and combinations thereof, may also be used. Ethers and esters including isodecyl neopentanoate, neopentylglycol heptanoate, glycol distearate, dicaprylyl carbonate, diethylhexyl carbonate, propylene glycol n-butyl ether (PnB), ethyl-3 ethoxypropionate, propylene glycol methyl ether acetate, tridecyl neopentanoate, propylene glycol methylether acetate (PGMEA), propylene glycol methyleether (PGME), octyldodecyl neopentanoate, diisobutyl adipate, diisopropyl adipate, propylene glycol dicaprylate/dicaprate, octyl palmitate, and combinations thereof, may also be used. Organic fats, oils, fatty acids, fatty alcohols, and combinations thereof, may also be used.

The carrier fluid typically has a viscosity of from 1-1,000, 2-50, or 5-50, alternatively 2-20, 2-15, 2-10, or 2-5, mm$^2$/s measured at 25° C. The carrier fluid is typically present in the pituitous silicone fluid in an amount of from 70-97, 75-95, 80-95, 85-95, 90-95, 93-95, 91-95, 92-94, or 92-93, parts by weight per 100 parts by weight of the pituitous silicone fluid. It is contemplated that any and all values or ranges of values between those described above may also be utilized.

The combination of the carrier fluid and the hydrosilylation reaction product provide the pituitous silicone fluid with a viscosity, measured in Pascal seconds (Pa·s) and collected relative to the shear rate in sec$^{-1}$, from 0.1-75, 0.3-15, 0.5-5, or 1-3, Pa·s. These viscosity values are typically measured using a controlled stress rheometer, such as the TA Instruments AR 1000-N. In various embodiments, the term "fluid", as used herein, describes a liquid whose component particles can move past one another, that is flow, when a force is applied, such as gravity. In this embodiment, "fluids" do not encompass "gels", which do not flow. In other embodiments, the pituitous silicone fluid has a viscosity of at least 100, at least 200, or at least 300, mPas (cP) at 23° C., each with a maximum of one of the values described above. It is contemplated that any and all values or ranges of values between those described above may also be utilized.

Emulsion:

The pituitous silicone fluid may be provided as an emulsion. As used herein, "emulsion" describes water continuous emulsions (for example an oil in water emulsion, or a silicone in water emulsion), oil or silicone continuous emulsions (water in oil emulsions or water in silicone emulsions), or multiple emulsions (water/oil/water, oil/water/oil types, water/silicone/water, or silicone/water/silicone). The pituitous silicone fluid may be provided as an emulsion using any techniques of the art, such as stirring, homogenizing, and sonalating, e.g. a batch, semi-continuous, or continuous process.

The amount of the pituitous silicone fluid used to form the emulsion can vary and is not limited. However, the amount typically may be from a vesicle/emulsion weight ratio of 0.1/99 to 99/0.1 or 1/99 to 99/1.

The emulsion may be w/o, w/s, or a multiple phase emulsion, as known in the art, e.g. using silicone emulsifiers. Typically a water-in-silicone emulsifier is utilized in such a formulation, is typically non-ionic, and is typically chosen from polyoxyalkylene-substituted silicones, silicone alkanolamides, silicone esters, silicone glycosides, and combinations thereof. Silicone-based surfactants may be used to form such emulsions, such as those described in U.S. Pat. Nos. 4,122,029, 5,387,417, and 5,811,487, each of which is expressly incorporated herein by reference in one or more non-limiting embodiments. Thickening agents may also be utilized, such as DOW CORNING® RM 2051.

In one embodiment, the emulsion is an oil in water emulsion and may include nonionic surfactants, such as polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, polyoxyalkylene glycol modified polysiloxane surfactants, and combinations thereof.

Optional Resin(s) and Polymer(s):

The composition may also include one or more of the following resins and/or copolymers. Alternatively, the hydrosilylation reaction product may be the reaction product of the first and second linear organopolysiloxanes, and one or more of the following resins and/or copolymers, e.g. in the presence of the hydrosilylation catalyst. The following resins and/or copolymers may also be used in the personal care compositions described further below and if so, they can be included in various amounts along with and/or separate from the composition.

In various embodiments, the composition includes an MQ resin. MQ resins are macromolecular polymers consisting essentially of $R_3SiO_{1/2}$ and $SiO_{4/2}$ units (the M and Q units, respectively) where R is a functional or nonfunctional organic group. Those skilled in the art appreciate that MQ resins may also include a limited number of D and T units. Specifically, the MQ resin may contain D and T units, provided that ≥80, or ≥90, mole % of the total siloxane units are M and Q units. Alternatively, the MQ resin may be free of D and/or T units.

The MQ resin can be an organosiloxane resin comprising siloxy units of the formula: $(R^1_3SiO_{1/2})_m(SiO_{4/2})_n$ where each $R^1$ is an independently selected substituted or unsubstituted hydrocarbyl group, "m" is ≥4, and "n" is ≥1. The ratio of m/n can vary, but is typically about 1.5-1, 0.6-1, or 0.9-1.

Suitable hydrocarbyl groups are described above. In certain embodiments, each $R^1$ is an independently selected alkyl group having from 1-8 carbon atoms, an aryl group, a carbinol group, or an amino group. The alkyl groups are generally illustrated by methyl, ethyl, propyl, butyl, pentyl, hexyl, and octyl, with the alkyl group typically being methyl. The aryl groups are generally illustrated by phenyl, naphthyl, benzyl, tolyl, xylyl, xenyl, methylpheny, 2-phenyethyl, 2-phenyl-2-methylethyl, corophenyl, bromophenyl and fluorophenyl, with the aryl group typically being phenyl.

A "carbinol group" is generally any group containing at least one carbon-bonded hydroxyl (COH) radical. Thus, the carbinol group may contain more than one COH radical, such as e.g.:

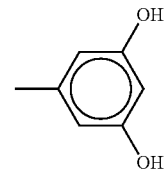

If free of aryl groups, the carbinol group typically has ≥3 carbon atoms. Such carbinol groups are generally illustrated by the formula: $R^4OH$ where $R^4$ is a divalent hydrocarbon or hydrocarbonoxy radical having ≥3 carbon atoms. $R^4$ is illustrated by alkylene radicals, such as by the formula: —(CH$_2$)$_x$— where x is 3-10; or by the formula: —CH$_2$CH(CH$_3$)—, —CH$_2$CH(CH$_3$)CH$_2$—, —CH$_2$CH$_2$CH(CH$_2$CH$_3$)CH$_2$CH$_2$CH$_2$—, or —OCH(CH$_3$)(CH$_2$)$_x$—, where x is 1-10.

An aryl-containing carbinol group typically has ≥6 carbon atoms. Such carbinol groups are generally illustrated by the formula: $R^5OH$ where $R^5$ is an arylene radical having from 6-14 carbon atoms. $R^5$ is illustrated by arylene radicals, such as by the formula: —(CH$_2$)$_x$C$_6$H$_4$— where x is 0-10; —CH$_2$CH(CH$_3$)(CH$_2$)$_x$C$_6$H$_4$— where x is 0-10; or —(CH$_2$)$_x$C$_6$H$_4$(CH$_2$)$_x$— where x is 1-10.

The amino group is illustrated by the formula: —R$^6$NH$_2$ or —R$^6$NHR$^7$NH$_2$ where each of R$^6$ and R$^7$ is independently a divalent hydrocarbon radical having ≥2 carbon atoms, typically each of $R^6$ and $R^7$ is independently an alkylene radical having from 2-20 carbon atoms. Each of $R^6$ and $R^7$ are independently illustrated by ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene. Typical amino groups include: —$CH_2CH_2CH_2NH_2$, —$CH_2(CH_3)CHCH_2(H)NCH_3$, —$CH_2CH_2NHCH_2CH_2NH_2$, —$CH_2CH_2NH_2$, —$CH_2CH_2NHCH_3$, —$CH_2CH_2CH_2CH_2NH_2$, —$(CH_2CH_2NH)_3H$, and —$CH_2CH_2NHCH_2CH_2NHC_4H_9$.

The MQ resin may also contain hydroxy groups. In various embodiments, the MQ resin has a total wt % hydroxy content of from 0-15, 1-12, 2-10, or 2-5, wt %. The MQ resin can also be further "capped" where residual hydroxy groups are reacted with additional M units.

MQ resins and methods for their preparation are known in the art. For example, U.S. Pat. No. 2,814,601 discloses that MQ resins can be prepared by converting a water-soluble silicate into a silicic acid monomer or silicic acid oligomer using an acid. When adequate polymerization has been achieved, the resin is end-capped with trimethylchlorosilane to yield the MQ resin. Another method for preparing MQ resins is described in U.S. Pat. No. 2,857,356, which discloses a method for the preparation of an MQ resin by the co-hydrolysis of a mixture of an alkyl silicate and a hydrolyzable trialkylsilane organopolysiloxane with water. Other suitable MQ resins and their methods of preparation are disclosed by U.S. Pat. Nos. 6,075,087, 7,452,849, 7,803,358, 8,012,544, and 8,017,712; and in WO2010065712 and WO2013117490. The aforementioned patents and publications are expressly incorporated herein by reference in one or more non-limiting embodiments. Suitable MQ resins are commercially available, such as DOW CORNING® MQ-1600 solid resin, MQ-1601 solid resin, MQ-1640 flake resin, 217 flake, and 5-7104.

If utilized, the MQ resin can be included in the composition in various amounts. In certain embodiments, the MQ resin is present in an amount of from about 0-99, 10-90, 30-90, or 40-80, parts by weight based on 100 parts by weight of the composition. Two or more different MQ resins may be utilized.

In various embodiments, the composition includes a copolymer. In certain embodiments, the copolymer may be referred to as an acrylate copolymer. Suitable acrylate copolymers are commercially available, such as DOW CORNING@ FA 4001 CM silicone acrylate and DOW CORNING@ FA 4002 ID silicone acrylate.

The acrylate copolymer can be formed by the reaction of a radically polymerizable organic monomer, which can be exemplified by: the esters of unsaturated carboxylic acids, such as methyl acrylate, ethyl acrylate, propyl acrylate, n-butyl acrylate, isobutyl acrylate, amyl acrylate, hexyl acrylate, 2-ethylhexyl acrylate, cyclohexyl acrylate, n-octyl acrylate, glycidyl acrylate, 2-hydroxyethyl acrylate, 2-hydroxypropyl acrylate, 2,2,3,3-tetrafluoropropyl acrylate, octafluoropentyl acrylate, methyl methacrylate, ethyl methacrylate, n-butyl methacrylate, isobutyl methacrylate, 2-ethylhexyl methacrylate, lauryl methacrylate, tridecyl methacrylate, benzyl methacrylate, cyclohexyl methacrylate, tetrahydrofurfuryl methacrylate, 2-hydroxyethyl methacrylate, 2-hydroxypropyl methacrylate, glycidyl methacrylate, 2-methoxyethyl methacrylate, 2-ethoxyethyl methacrylate, and octafluoropentyl methacrylate; unsaturated aliphatic carboxylic acids, such as methacrylic acid and acrylic acid; the amides of unsaturated aliphatic carboxylic acids, such as acrylamide, methacrylamide, and N-methylolacrylamide; unsaturated aliphatic nitriles, such as acrylonitrile and methacrylonitrile; unsaturated aliphatic compounds, such as vinyl acetate, vinyl propionate, and vinyl versatate; unsaturated carboxylic acid anhydrides, such as maleic anhydride and 4-methacryloxyethyltrimellitic anhydride (4-META); vinyl halides, such as vinyl chloride and vinyl fluoride; aromatic vinyl compounds, such as styrene, methylstyrene, vinyltoluene and vinylpyridine; and aliphatic dienes, such as butadiene and isoprene.

The copolymer may be a carbosiloxane dendrimer, such as those described and prepared in U.S. Pat. No. 6,306,992, which is expressly incorporated herein by reference in one or more non-limiting embodiments. Examples of suitable carbosiloxane dendrimers include those represented by the general formula:

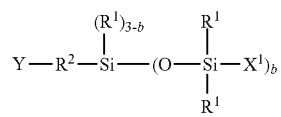

where each $R^1$ is independently a 1-10 carbon alkyl or aryl group; $R^2$ is a divalent organic group excluding 1-10 carbon alkylene groups; "b" is 1-3; and $X^1$ is a silylalkyl group represented by the following general formula (when "i"=1):

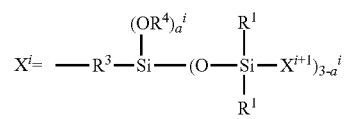

where $R^1$ is defined as above; $R^3$ is a 2-10 carbon alkylene group; $R^4$ is a 1-10 carbon alkyl group; $X^{i+1}$ is selected from hydrogen, a 1-10 carbon alkyl group, an aryl group, and the $X^1$ silylalkyl group; "i" indicates a generation number of the $X^1$ silylalkyl group above and is 1-10; $a^i$ is 0-3; and Y is a radically-polymerizable group. The radically-polymerizable group is typically selected from: a 2-10 carbon alkenyl group; groups with the following general formula:

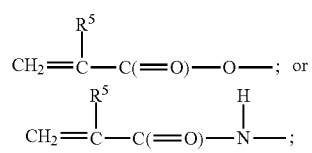

groups with the following formula:

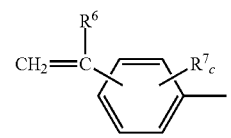

where each of $R^5$ and $R^6$ is independently hydrogen or Me; $R^7$ is a 1-10 carbon alkyl group; and "c" is 0-4.

The copolymer may be a branched siloxane-silalkylene copolymer, such as those described and prepared in U.S. Pat. No. 6,420,504, which is expressly incorporated herein by reference in one or more non-limiting embodiments.

Examples of suitable branched siloxane-silalkylene copolymers include those represented by the general formula:

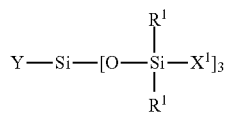

where $R^1$ is defined as above; and $X^1$ is a silylalkyl group represented by the following general formula (when "i"=1):

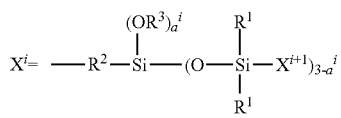

where $R^1$ is defined as above; $R^2$ is a 2-10 carbon alkylene group; $R^3$ is a 1-10 carbon alkyl group; and $X^{i+1}$ is selected from hydrogen, a 1-10 carbon alkyl group, an aryl group, and the $X^1$ silylalkyl group above; "i" indicates a generation number of the $X^1$ silylalkyl group above and is 1-10; and $a^i$ is from 0-3. Y is a radical-polymerizable group. The radically-polymerizable group is typically selected from: a 2-10 carbon alkenyl group; a (meth)-acryl group-containing organic group represented by the following general formula:

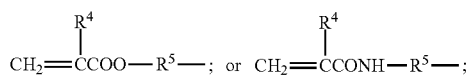

a styryl group-containing organic group represented by the following general formula:

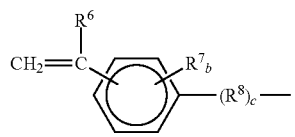

where each of $R^4$ and $R^6$ is independently hydrogen or Me; each of $R^5$ and $R^8$ is independently a 1-10 carbon alkylene group; $R^7$ is a 1-10 carbon alkyl group; "b" is 0-4; and "c" is 0 or 1.

If utilized, the copolymer can be included in the composition in various amounts. In certain embodiments, the copolymer in present in an amount of from about 0-99, 10-90, 30-90, or 40-80, parts by weight based on 100 parts by weight of the composition. Two or more different copolymers may be utilized.

Method of Forming the Pituitous Silicone Fluid:

This disclosure also provides a method of forming the pituitous silicone fluid. The method includes reacting the first and second linear organopolysiloxanes via a hydrosilylation reaction in the presence of the hydrosilylation catalyst and the carrier fluid to form the pituitous silicone fluid, e.g. a hydrosilylation reaction product including alkenyl or Si—H functionality. The method may include the step of combining the first linear organopolysiloxane, second linear organopolysiloxane, hydrosilylation catalyst, and carrier fluid, prior to reaction. Typically, the pituitous silicone fluid is not formed 100% neat. Instead, the pituitous silicone fluid is typically formed directly at a final solids content in the presence of the carrier fluid and/or formed at a higher solids content and then diluted with additional carrier fluid to the desired lower end use solids level. In other words, the method may include the step of adding additional carrier fluid to the pituitous silicone fluid and/or to the hydrosilylation reaction product.

Personal Care Composition:

This disclosure also provides a personal care composition, which may also be described as a personal care product composition. The personal care composition includes the pituitous silicone fluid described above. The personal care composition may be in the form of a cream, a gel, a powder, a paste, or a freely pourable liquid. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments, such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art.

The personal care composition can be used in or for a variety of personal, household, and healthcare applications. In particular, the pituitous silicone fluid and/or personal care compositions of the present disclosure may be used in the personal care products as described in U.S. Pat. Nos. 6,051, 216, 5,919,441, 5,981,680; WO2004/060271 and WO2004/060101; in sunscreen compositions as described in WO2004/060276; in cosmetic compositions also containing film-forming resins, as described in WO03/105801; in the cosmetic compositions as described in US Pub. Nos. 2003/0235553, 2003/0072730 and 2003/0170188, in EP Pat. Nos. 1,266,647, 1,266,648, and 1,266,653, in WO03/105789, WO2004/000247 and WO03/106614; as additional agents to those described in WO2004/054523; in long wearing cosmetic compositions as described in US Pub. No. 2004/0180032; and/or in transparent or translucent care and/or make up compositions as described in WO2004/054524; all of which are expressly incorporated herein by reference in various non-limiting embodiments.

The personal care composition and/or pituitous silicone fluid can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care composition and/or pituitous silicone fluid may be used in a conventional manner for example for conditioning the skin. An effective amount of the personal care composition and/or pituitous silicone fluid may be applied to the skin. Such effective amounts are generally from 1-3 mg/cm$^2$. Application to the skin typically includes working the personal care composition and/or pituitous silicone fluid into the skin. This method for applying to the skin typically includes the steps of contacting the skin with the personal care composition and/or pituitous silicone fluid in an effective amount and then rubbing the personal care composition and/or pituitous silicone fluid into the skin. These steps can be repeated as many times as desired to achieve the desired benefit.

Use of the personal care composition and/or pituitous silicone fluid on hair may use a conventional manner for conditioning hair. An effective amount of the personal care composition and/or pituitous silicone fluid for conditioning hair is applied to the hair. Such effective amounts are generally from 1-50, or 1-20, grams (g). Application to the hair typically includes working the personal care composition and/or pituitous silicone fluid through the hair such that most or all of the hair is contacted with the personal care composition and/or pituitous silicone fluid. This method for conditioning the hair typically includes the steps of applying an effective amount of the personal care composition and/or pituitous silicone fluid to the hair, and then working the personal care composition and/or pituitous silicone fluid through the hair. These steps can be repeated as many times as desired to achieve the desired conditioning benefit.

Non-limiting examples of additives which may be formulated into the personal care composition and/or pituitous silicone fluid include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-carie and wound healing-promotion agents.

The personal care composition, such as a shampoo or cleanser, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids, such as sulfonated monoglycerides of coconut oil acids, salts of sulfonated monovalent alcohol esters, such as sodium oleylisethianate, amides of amino sulfonic acids, such as the sodium salt of oleyl methyl tauride, sulfonated products of fatty acids nitriles, such as palmitonitrile sulfonate, sulfonated aromatic hydrocarbons, such as sodium α-naphthalene monosulfonate, condensation products of naphthalene sulfonic acids with formaldehyde, sodium octahydroanthracene sulfonate, alkali metal alkyl sulfates, such as sodium lauryl sulfate, ammonium lauryl sulfate or triethanol amine lauryl sulfate, ether sulfates having alkyl groups of eight or more carbon atoms, such as sodium lauryl ether sulfate, ammonium lauryl ether sulfate, sodium alkyl aryl ether sulfates, and ammonium alkyl aryl ether sulfates, alkylarylsulfonates having one or more alkyl groups of eight or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the personal care composition in an amount of from 5-50, or 5-25, wt % based on the total weight of the personal care composition.

The personal care composition may include at least one cationic deposition aid, typically a cationic deposition polymer. The cationic deposition aid is typically present at levels of from 0.001-5, 0.01-1, or 0.02-0.5, % by weight. The cationic deposition polymer may be a homopolymer or be formed from two or more types of monomers. The molecular weight of the cationic deposition polymer is typically from 5,000-10,000,000, 10,000-5,000,000, or 100,000-2,000,000. The cationic deposition polymers typically have cationic nitrogen containing groups, such as quaternary ammonium or protonated amino groups, or a combination thereof. The cationic charge density should be at least 0.1 meq/g, and is typically above 0.8 or higher. The cationic charge density should not exceed 4 meq/g, and it is typically <3 meq/g and more typically <2 meq/g. The charge density can be measured using the Kjeldahl method and is within the above limits at the desired pH of use, which will in general be from 3-9 or 4-8. It is contemplated that any and all values or ranges of values between those described above may also be utilized.

The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers, such as (meth)acrylamide, alkyl and dialkyl (meth)acrylamides, alkyl (meth)acrylate, vinyl caprolactone and vinyl pyrrolidine. The alkyl and dialkyl substituted monomers typically have $C_1$-$C_7$ alkyl groups, more typically $C_1$-$C_3$ alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the personal care composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings, such as pyridinium, imidazolium, and quaternized pyrrolidine, e.g. alkyl vinyl imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls, such as the $C_1$-$C_7$ alkyls, more typically $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically $C_1$-$C_7$ hydrocarbyls, more typically $C_1$-$C_3$ alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquaternium-16), such as those commercially available from BASF Corp. (Florham Park, N.J., USA) under the LUVIQUAT trade name (e.g. LUVIQUAT FC 370); copolymers of 1-vinyl-2-pyrrolidine and dimethylaminoethyl methacrylate (referred to in the industry by CTFA as Polyquaternium-11), such as those commercially from Gar Corporation (Wayne, N.J., USA) under the GAFQUAT trade name (e.g. GAFQUAT 755N); cationic diallyl quaternary ammonium-containing polymer including, for example, dimethyl diallyammonium chloride homopolymer and copolymers of acrylamide and dimethyl diallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3-5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments. Other cationic deposition aids that can be used include polysaccharide polymers, such as cationic cellulose derivatives and cationic starch derivatives. Cationic polysaccharide polymer materials suitable for use in the personal care compositions include those of the formula: A-O(R—N+$R^1R^2R^3X^-$) where "A" is an anhydroglucose residual group, such as starch or cellulose anhydroglucose residual; R is an alkylene oxyalklene, polyoxyalkylene, or hydroxyalkylene group, or combination thereof; $R^1$, $R^2$ and $R^3$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^1$, $R^2$, and $R^3$) typically being 20; and X is an anionic counterion. Examples of such anionic counterions include: halides (e.g., chloride, fluoride, bromide, iodide), sulfate, methylsulfate, phosphate, monohydrogen phosphate, nitrate, and the like. Cationic cellulose is available from Amerchol Corp. (Edison, N.J., USA) in their Polymer iR™ and Polymer LR™ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, and bis(2-hydroxyethyl) $C_{12}$-$C_{15}$ alkoxypropylamine oxide. Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the personal care compositions in an amount of from 1-15, or 2-10, wt % based on the total weight of the personal care composition. The personal care composition may further include a polyalkylene glycol to improve lather performance. Concentration of the polyalkylene glycol in the personal care composition may be from 0.01-5, 0.05-3, or 0.1-2, % by weight of the personal care composition. The optional polyalkylene glycols are characterized by the general formula: H(OCH$_2$CHR)$_n$—OH where R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, "n" has an average value of from 1,500-25,000, 2,500-20,000, or 3,500-15,000. Polyethylene glycol polymers useful herein are PEG-2M wherein R equals H and "n" has an average value of 2,000 (PEG-2M is also known as Polyox WSR9N-10, which is available from Union Carbide and as PEG-2,000); PEG-5M wherein R equals H and "n" has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and "n" has an average value of 7,000 (PEG-7M is also known as Polyox WSRO N-750 available from Union Carbide); PEG-9M wherein R equals H and "n" has an average value of 9,000 (PEG 9-M is also known as Polyox WSRS N-3333 available from Union Carbide); and PEG-14 M wherein R equals H and "n" has an average value of 14,000 (PEG-14M is also known as Polyox WSRO N-3000 available from Union Carbide). Other useful polymers include the polypropylene glycols and mixed polyethylene/polypropylene glycols.

The personal care composition may include a suspending agent at concentrations effective for suspending a silicone conditioning agent, or other water-insoluble material, in dispersed form in the personal care composition. Such concentrations may be from 0.1-10, or 0.3-5.0, % by weight of the personal care composition. Suspending agents include crystalline suspending agents which can be categorized as acyl derivatives, long chain amine oxides, and combinations thereof, concentrations of which can be from 0.1-5.0, or 0.5-3.0, % by weight of the personal care compositions. These suspending agents are described in U.S. Pat. No. 4,741,855, which is expressly incorporated herein by reference in one or more non-limiting embodiments. These typical suspending agents include ethylene glycol esters of fatty acids typically having from 16-22 carbon atoms. More typical are the ethylene glycol stearates, both mono and distearate, but particularly the distearate containing less than 7% of the mono stearate. Other suitable suspending agents include alkanol amides of fatty acids, typically having from 16-22 carbon atoms, more typically 16-18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having $C_8$-$C_{22}$ chains may be used. Other long chain acyl derivatives suitable for use as suspending agents include N,N-dihydrocarbyl amido benzoic acid and soluble salts thereof (e.g. Na, K), particularly N,N-di(hydrogenated) $C_{16}$, $C_{18}$ and tallow amido benzoic acid species of this family, which are commercially available from Stepan Company (Northfield, Ill., USA). Examples of suitable long chain amine oxides for use as suspending agents include alkyl ($C_{16}$-$C_{22}$) dimethyl amine oxides, e.g. stearyl dimethyl amine oxide. Other suitable suspending agents include xanthan gum at concentrations ranging from 0.3-3, or 0.4-1.2, % by weight of the personal care compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the personal care compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid crosslinked with polyallylsucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow) phthalic acid amide, and cross-linked maleic anhydride-methyl vinyl ether copolymer. Other suitable suspending agents may be used in the personal care compositions, including those that can impart a gel-like viscosity to the personal care composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition may include one or more water-soluble emollients including, but not limited to, lower molecular weight aliphatic diols, such as propylene glycol and butylene glycol; polyols, such as glycerine and sorbitol; and polyoxyethylene polymers, such as polyethylene glycol 200. The specific type and amount of water soluble emollient(s) employed will vary depending on the desired aesthetic characteristics of the personal care composition, and is readily determined by one skilled in the art.

The personal care composition may include one or more oils independent from the carrier fluid described above. The term "oil" as used herein describes any material which is substantially insoluble in water. Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate and silicones especially cyclomethicone and dimethicone and combinations thereof. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity surface oils generally have a viscosity of 200-1,000,000, or 100,000-250,000, mPas at 25° C. Surface oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is 1:15 to 15:1, or 1:10 to 10:1, respectively. Example formulations of this disclosure include 1-20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojaba, olive or cereal germ oil, may be utilized. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition may include various waxes. The waxes generally have a melting point of from 35-120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition may include a powder. The powder can be generally defined as dry, particulate matter having a particle size of 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature. Specific examples of suitable powders include DOW CORNING® 9506 and 9701, cosmetic powders.

The powder can also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a combination with colored pigments, or some organic dyes, generally used as a combination with colored pigments and commonly used in the cosmetics industry, can be added to the personal care composition. In general, these coloring agents can be present in an amount by weight from 0-20% with respect to the weight of the personal care composition.

Pulverulent inorganic or organic fillers can also be added, generally in an amount by weight from 0-40% with respect to the weight of the personal care composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be cross-linked. The fillers may typically be present in a proportion of from 0-35, or more typically 5 to 15, % of the total weight of the personal care composition. Mention may be made in particular of talc, mica, silica, kaolin, nylon powders (in particular ORGASOL), polyethylene powders, Teflon, starch, boron nitride, copolymer microspheres, such as EXPANCEL (Nobel Industrie), polytrap and silicone resin microbeads (TOSPEARL from Toshiba, for example).

The personal care composition may include a sunscreen. Sunscreens typically absorb ultraviolet light between 290-320 nanometers (the UV-B region), such as, but not exclusively, para-aminobenzoic acid derivatives and cinnamates, such as octyl methoxycinnamate and those which absorb ultraviolet light in the range of 320-400 nanometers (the UV-A region), such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. In various embodiments, the sunscreen is as described in EP-A-678,292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one $SO_3H$ group, mention may be made more particularly of 3-benzylidine-2-camphorsulphonic derivatives. A particularly typical compound is benzene-1,4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl)benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy)benzylidenecamphor-10-sulphonic acid, 3-(4-methoxy)benzylidenecamphor-10-sulphonic acid, 3-(4,5-dimethoxy)benzylidenecamphor-10-sulphonic acid, 3-(4-n-butoxy)benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597 and FR Pat. Nos. 2,236,515, 2,282,426, 2,645,148, 2,430,938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the personal care composition in a content which can be from 0.1-20, or 0.2-10, % by weight relative to the total weight of the personal care composition.

Additional lipophilic screening agents can be utilized, such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in this disclosure, mention may also be made of p-methylbenzylidenecamphor, which is also known as a UV-B absorber and is sold in particular under the trade name "Eusolex 6300" by Merck. The lipophilic screening agent(s) can be present in the personal care composition in a content which can be from 0.5-30, or 0.5-20, % of the total weight of the personal care composition. Other examples of lipophilic or hydrophilic organic screening agents are described in patent application EP-A-0,487,404, which is expressly incorporated herein by reference in one or more non-limiting embodiments. The personal care compositions can also include pigments or alternatively nanopigments (average primary particle size: generally between 5-100, or 10-50, nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum stearate, and silicones. Such coated or uncoated metal oxide nanopigments are described in particular in patent applications EP-A-0,518,772 and EP-A-0,518,773, each of which is expressly incorporated herein by reference in one or more non-limiting embodiments.

A thickening agent may be utilized in the personal care composition to provide a convenient viscosity. For example, viscosities of from 500-25,000, or 3,000 to 7,000, mm$^2$/s at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellu lose, starch, and starch derivatives exemplified by hydroxyethylamylose and starch amylose, locust bean gum, electrolytes exemplified by sodium chloride and ammonium chloride, and saccharides, such as fructose and glucose, and derivatives of saccharides, such as PEG-120 methyl glucose diolate or combinations of two or more of these. Alternatively, the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, when used in the personal care composition, may provide a viscosity of from 500-25,000 mm$^2$/s at 25° C. Alternatively, the thickening agent may be present in an amount of from 0.05-10, or 0.05-5, wt % based on the total weight of the personal care composition.

Stabilizing agents can also be used, e.g. in a water phase of an emulsion. Suitable water phase stabilizing agents can include alone or in combination one or more electrolytes, polyols, alcohols, such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1-5, or 0.5 to 3, wt % of the personal care composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

The emulsion can be used in personal care compositions, such as antiperspirant and deodorant compositions, under but not limited to the form of sticks, soft solid, roll on, aerosol, and pumpsprays. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care composition can be an aerosol in combination with propellant gases, such as carbon dioxide, nitrogen, nitrous oxide, volatile hydrocarbons, such as butane, isobutane, or propane and chlorinated or fluorinated hydrocarbons, such as dichlorodifluoromethane and dichlorotetrafluoroethane or dimethylether.

Silicone compositions, other than the present pituitous silicone fluid compositions and the carrier fluid, may also be included in the personal care compositions. For example, such silicones include silicone fluids, gums, resins, elastomers; silicone surfactants and emulsifiers, such as silicone polyethers, organofunctional silicones, such as amino functional silicones and alkylmethylsiloxanes. Alkylmethylsiloxanes may be included in the personal care compositions. These siloxane polymers generally have the formula: $Me_3SiO[Me_2SiO]_y[MeRSiO]_zSiMe_3$ where R is a hydrocarbon group containing 6-30 carbon atoms, Me represents methyl, and the degree of polymerization (DP or dp), i.e., the sum of y and z is 3-50. Both the volatile and liquid species of alkylmethylsiloxanes can be used in the personal care composition.

Silicone gums other than those described above may also be included in the personal care compositions. Suitable non-limiting gums include insoluble polydiorganosiloxanes having a viscosity >1,000,000, or >5,000,000, mm$^2$/s at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity >5 million and 20 million, mm$^2$/s at 25° C. Compositions of this type in are described for example in U.S. Pat. No. 6,013,682, which is expressly incorporated herein by reference in one or more non-limiting embodiments.

Silicone resins may also be included in the personal care composition. These resins are generally highly cross-linked polymeric siloxanes. Crosslinking is typically obtained by incorporating trifunctional and/or tetrafunctional silanes with the monofunctional silane and/or difunctional silane monomers used during manufacture. The degree of crosslinking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be used. Commercially available silicone resins suitable for applications herein are generally supplied in an unhardened form in low viscosity, volatile or nonvolatile silicone fluids. The silicone resins may be incorporated into the personal care compositions in their non-hardened forms rather than as hardened resinous structures.

Silicone carbinol fluids may be included in the personal care composition. These materials can be commonly described as substituted hydrocarbyl functional siloxane fluids or resins and some are described in WO003/101412, which is expressly incorporated herein by reference in one or more non-limiting embodiments.

Water soluble or water dispersible silicone polyethers may also be included in the personal care composition. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Additional Components:

The personal care composition and/or the pituitous silicone fluid and/or the composition as a whole may also include a solvent, such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, n-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as mineral oil, gasoline, naphtha, kerosene, gas oil, heavy oil, and crude oil; lubricating oils, such as spindle oil and turbine oil; and fatty oils, such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents, such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils, such as lemon, orange, lime, and grapefruit; fruit essences, such as apple, pear, peach, grape, strawberry, raspberry, cherry, plum, pineapple, and apricot; and other useful flavoring agents including aldehydes and esters, such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances, such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals, such as amyl salicylate, amyl cinnamic aldehyde, benzyl acetate, citronellol, coumarin, geraniol, isobornyl acetate, ambrette, and terpinyl acetate; and the various classic family perfume oils, such as the floral bouquet family, oriental family, chypre family, woody family, citrus family, canoe family, leather family, spice family, and herbal family.

Method of Forming the Personal Care Composition:

This disclosure also provides a method of forming the personal care composition. The method includes combining a personal care product or any other similar compound, as described above, with the pituitous silicone fluid. It is contemplated that the personal care product may be present before, during, and/or after reaction of the first and second linear organopolysiloxanes. In one embodiment, the pituitous silicone fluid is prepared individually and then combined later with the personal care composition ingredients. It is possible to include some personal care ingredients at a fluid reaction step (i.e., formation of the hydrosilylation reaction product) but various factors may need to be controlled, such as reaction inhibition, temperature sensitivity of the ingredients, etc. Techniques known in the art for formation of personal care formulations, including but not limited to, mixing techniques, cold blends or application of heat to facilitate forming the personal care composition, can be used. The order of addition used herein can be any known in the art.

This disclosure also provides a method of imparting pituitous properties to a carrier fluid. The method includes the step of reacting the first and second linear organopolysiloxanes via a hydrosilylation reaction in the presence of the hydrosilylation catalyst and the carrier fluid to form the hydrosilylation reaction product including the alkenyl or Si—H functionality. This method may also include one or more method steps as described above.

EXAMPLES

Example 1: Hydrosilylation Reaction Product—4 wt % in Carrier Fluid

Into a reaction flask, the following raw materials were loaded: 7.72 g of 830DP vinyl terminated siloxane (i.e., dimethyl siloxanes, dimethylvinyl terminated), 0.344 g of 100DP siloxane with 6 pendant SiH sites (i.e., dimethyl, methylhydrogen siloxane, trimethylsiloxy terminated), 191.92 g of 2 cSt polydimethylsiloxane, and 0.080 g of platinum catalyst solution (which is approximately 2.0 ppm of Pt relative to the total batch size). Agitation began and reaction flask was heated to 75° C. After approximately 20 minutes of reaction time, stirring was stopped, as the reaction mixture had become increasingly viscous. The product was held static for an additional two hours at 75° C.

Figure 5:
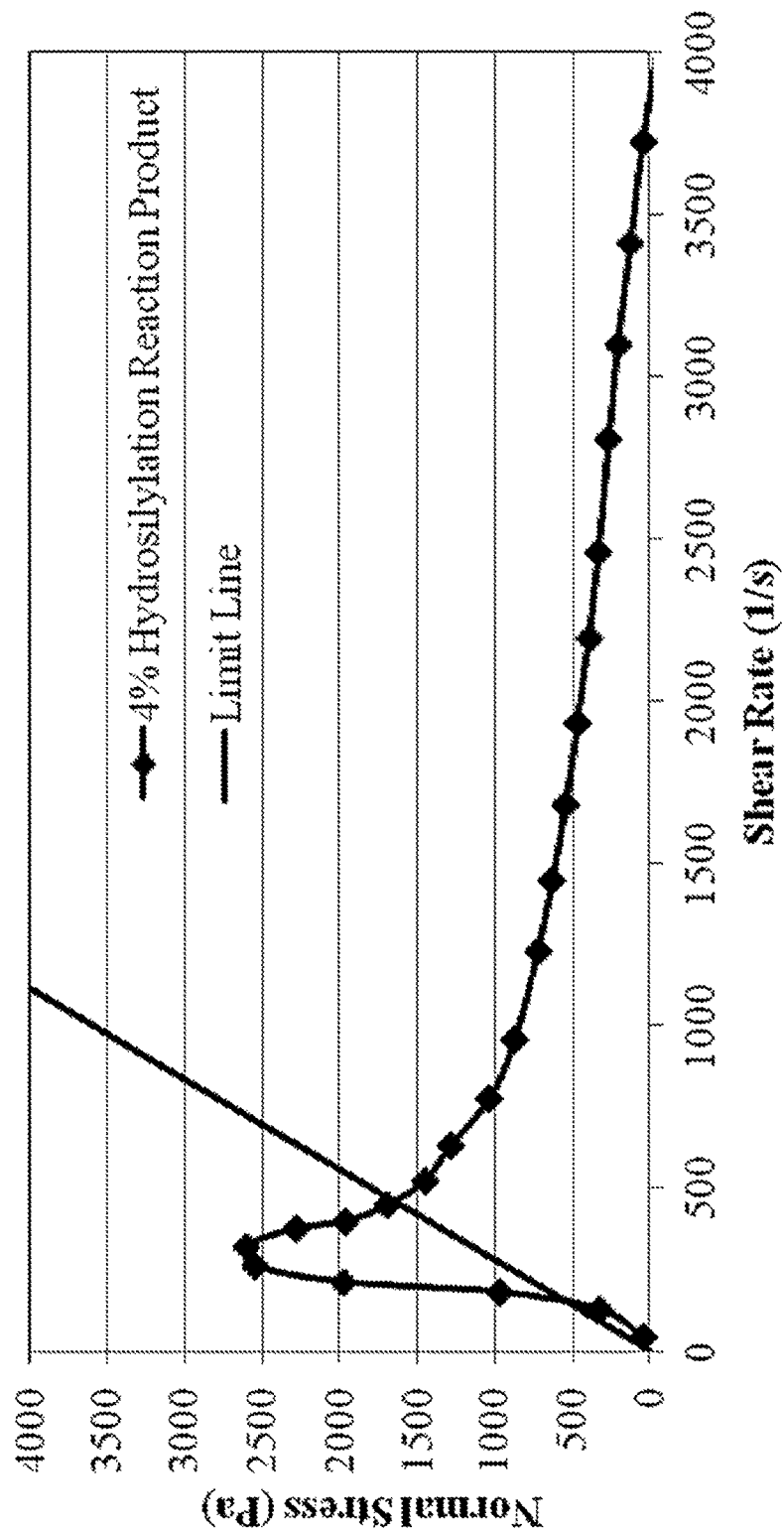
FIG. 5 is a line graph of stress as a function of shear of the pituitous silicone fluid of Example 1.

Once the reaction was complete, the product was allowed to cool to room temperature prior to characterization. The material was measured on a TA Instruments AR 1000-N controlled force rheometer, which is also used to measure other materials described below. FIG. 5 sets forth a plot of the Normal Stress (Pa) versus the Shear Rate (1/sec) for the pituitous silicone fluid described above.

Example 2: Hydrosilylation Reaction Product—15 wt % in Carrier Fluid

Into a reaction flask, the following raw materials were loaded: 30.0 g of the 830DP vinyl terminated siloxane described above, 0.650 g of the 100DP siloxane with 6 pendant SiH sites described above, 175.85 g of the 2 cSt polydimethylsiloxane, and 0.164 g of the platinum catalyst described above (which is approximately 4.0 ppm of Pt relative to the total batch size). Agitation began and reaction flask was heated to 75° C. After approximately 90 minutes of reaction time, stirring was stopped as the reaction mixture became increasingly viscous. The reaction mixture was held static for an additional two hours at 75° C., and then the catalyst was inhibited with 0.32 g of a 1% solution of triphenylphosphine in the 2 cSt polydimethylsiloxane.

Figure 6:
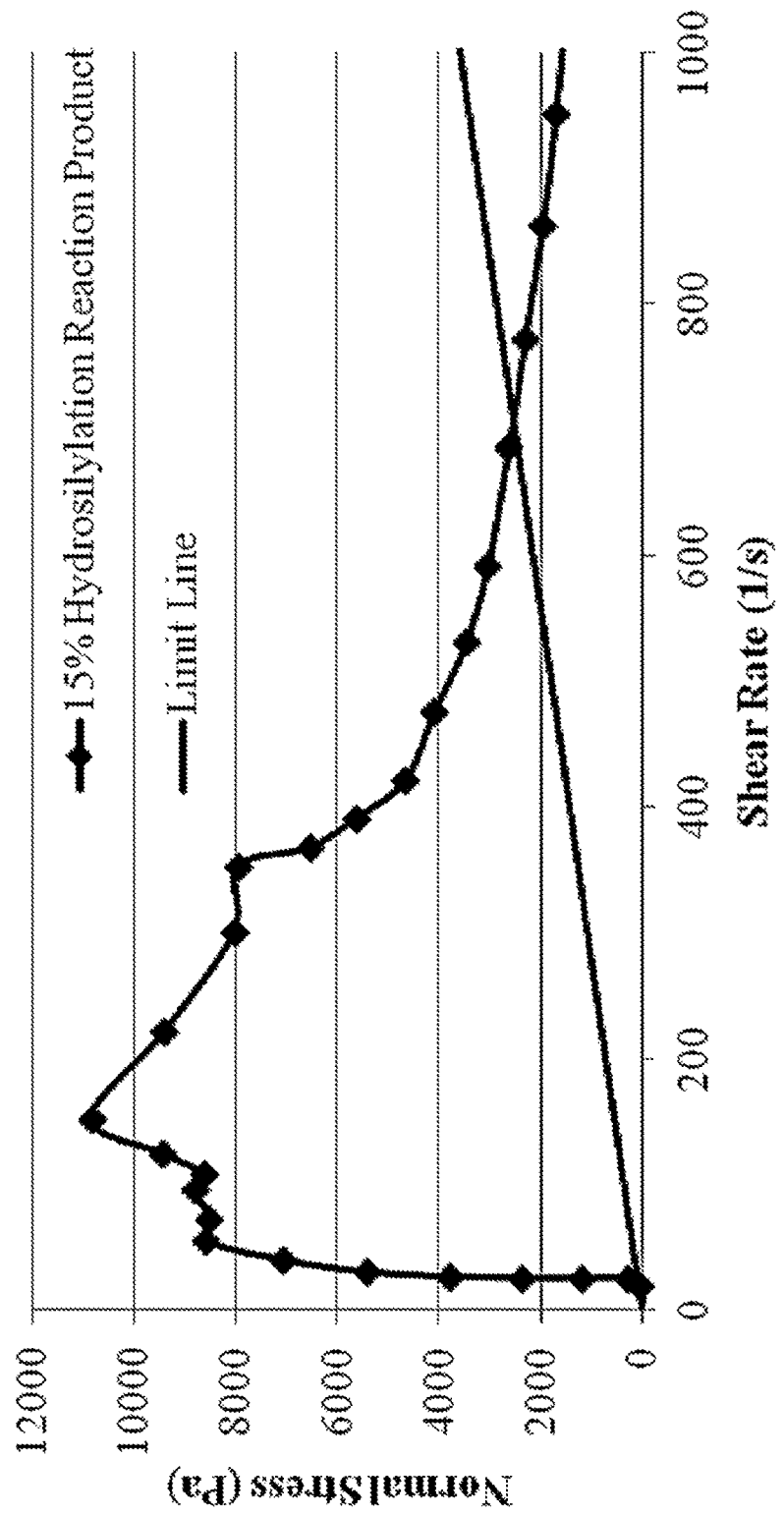
FIG. 6 is a line graph of stress as a function of shear of the pituitous silicone fluid of Example 2.

Once the reaction was complete, the product was allowed to cool to room temperature prior to characterization. FIG. 6 sets forth a plot of the Normal Stress (Pa) versus the Shear Rate (1/sec) for the pituitous silicone fluid described above.

Example 3: Hydrosilylation Reaction Product—6.25 wt % in Carrier Fluid

Into a reaction flask, the following raw materials were loaded: 12.44 g of a 9,502DP vinyl terminated siloxane (i.e., dimethyl siloxanes, dimethylvinyl terminated), 0.134 g of the 100DP siloxane with 6 pendant SiH sites described above, 187.42 g of the 2 cSt polydimethylsiloxane; and 0.080 g of the platinum catalyst solution described above (which is approximately 2.0 ppm of Pt relative to the total batch size). Agitation began and the reaction flask was heated to 75° C. After approximately 40 minutes of reaction time, stirring was stopped, as the reaction mixture had become increasingly viscous. The product was held static for an additional two hours at 75° C.

Figure 7:
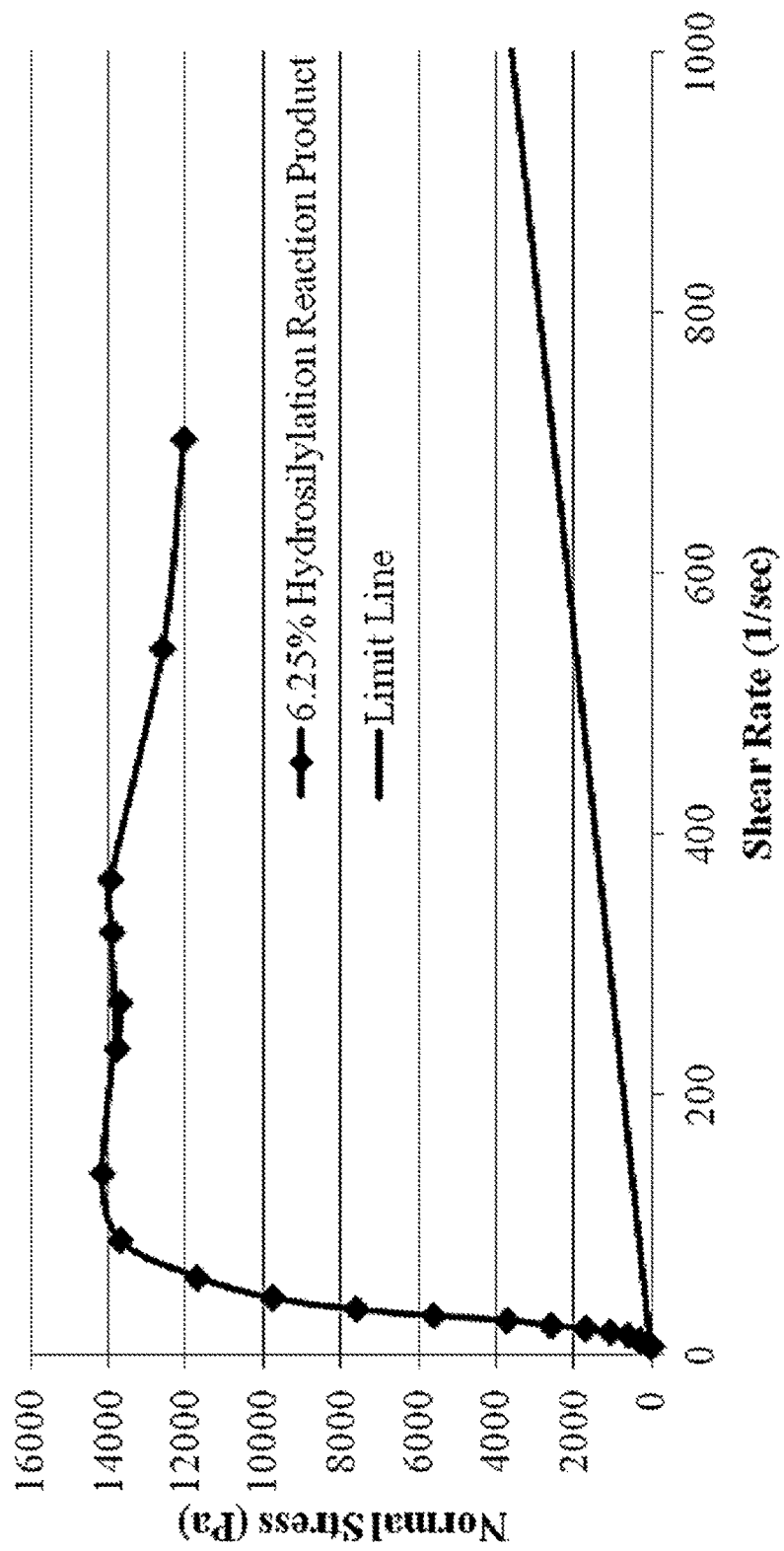
FIG. 7 is a line graph of stress as a function of shear of the pituitous silicone fluid of Example 3.

Once the reaction was complete, the product was allowed to cool to room temperature prior to characterization. FIG. 7 sets forth a plot of the Normal Stress (Pa) versus the Shear Rate (1/sec) for the pituitous silicone fluid described above.

Example 4: Hydrosilylation Reaction Product—8.5 wt % in Carrier Fluid

Into a reaction flask, the following raw materials were loaded: 2.74 g of 160DP dimethyl, methylvinyl siloxanes, trimethylsiloxy terminated, 15.27 g of 350DP siloxane with terminal SiH sites (i.e., dimethyl siloxanes, hydrogen terminated), 182.94 g of the 2 cSt polydimethylsiloxane, and 0.080 g of the platinum catalyst solution (which is approximately 2.0 ppm of Pt relative to the total batch size). Agitation began and the reaction flask was heated to 75° C. After approximately 6 hours of reaction time, stirring was stopped, as the reaction mixture had become increasingly viscous. Product was held static for an additional two hours at 75° C.

Figure 8:
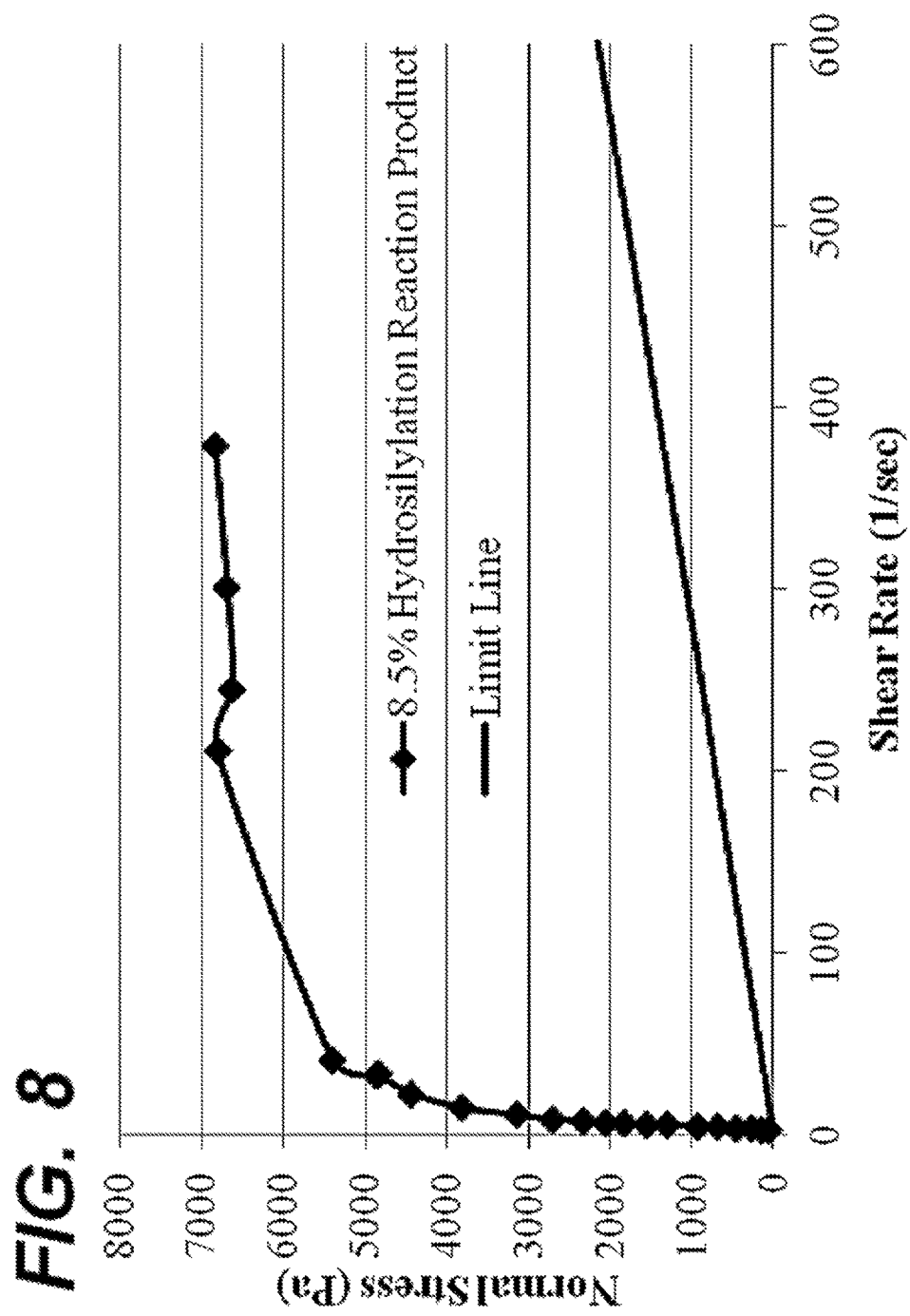
FIG. 8 is a line graph of stress as a function of shear of the pituitous silicone fluid of Example 4.

Once the reaction was complete, the product was allowed to cool to room temperature prior to characterization. FIG. 8 sets forth a plot of the Normal Stress (Pa) versus the Shear Rate (1/sec) for the pituitous silicone fluid described above.

Example 5: Hydrosilylation Reaction Product—10 wt % in Carrier Fluid

Concentrated Gel:

Into a reaction flask, the following raw materials were loaded: 4.89 g of the 830DP vinyl terminated siloxane described above, 0.194 g of the 100DP siloxane with 6 pendant SiH sites described above, 47.26 g of the 2 cSt polydimethylsiloxane, and 0.042 g of the platinum catalyst solution described above (which is approximately 4.0 ppm of Pt relative to the total batch size). The contents were mixed at 2,500 RPM for 30 seconds on a dental mixer and then placed in a 70° C. oven for 18 hours to cure. The resulting product was a firm gel at an active silicone gel content of 10 wt % in the 2 cSt polydimethylsiloxane.

Dilution and Shear:

The firm gel was further diluted down to 7 wt % and 5 wt % with additional amounts of the 2 cSt polydimethylsiloxane. To achieve 7 wt %, 14.0 g of the firm gel and 6.0 g of the 2 cSt polydimethylsiloxane were loaded into a dental mixer cup and mixed at 2,500 RPM for 30 seconds in a dental mixer. A serial dilution was performed as 10.0 g of the resulting product at 7 wt % was mixed with 10.0 g of the 2 cSt polydimethylsiloxane, at 2,500 RPM for 30 seconds in a dental mixer to produce a 3.5 wt % sample. To achieve 5 wt %, 10.0 g of the firm gel and 10.0 g of the 2 cSt polydimethylsiloxane were loaded into a dental mixer cup and mixed at 2,500 RPM for 30 seconds in a dental mixer.

Figure 9A:
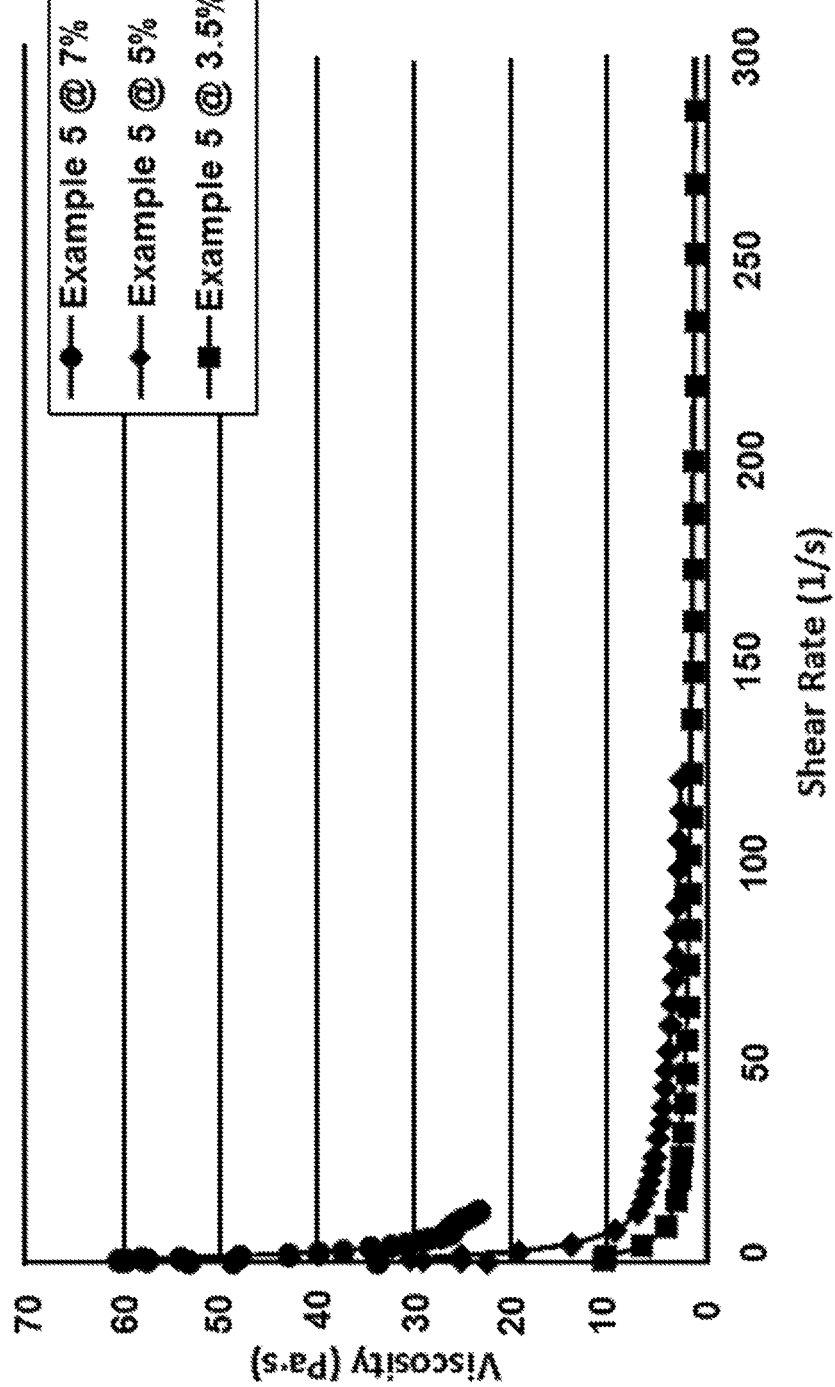
FIG. 9A is a line graph of viscosity as a function of shear of the pituitous silicone fluid of Example 5.
Figure 9B:
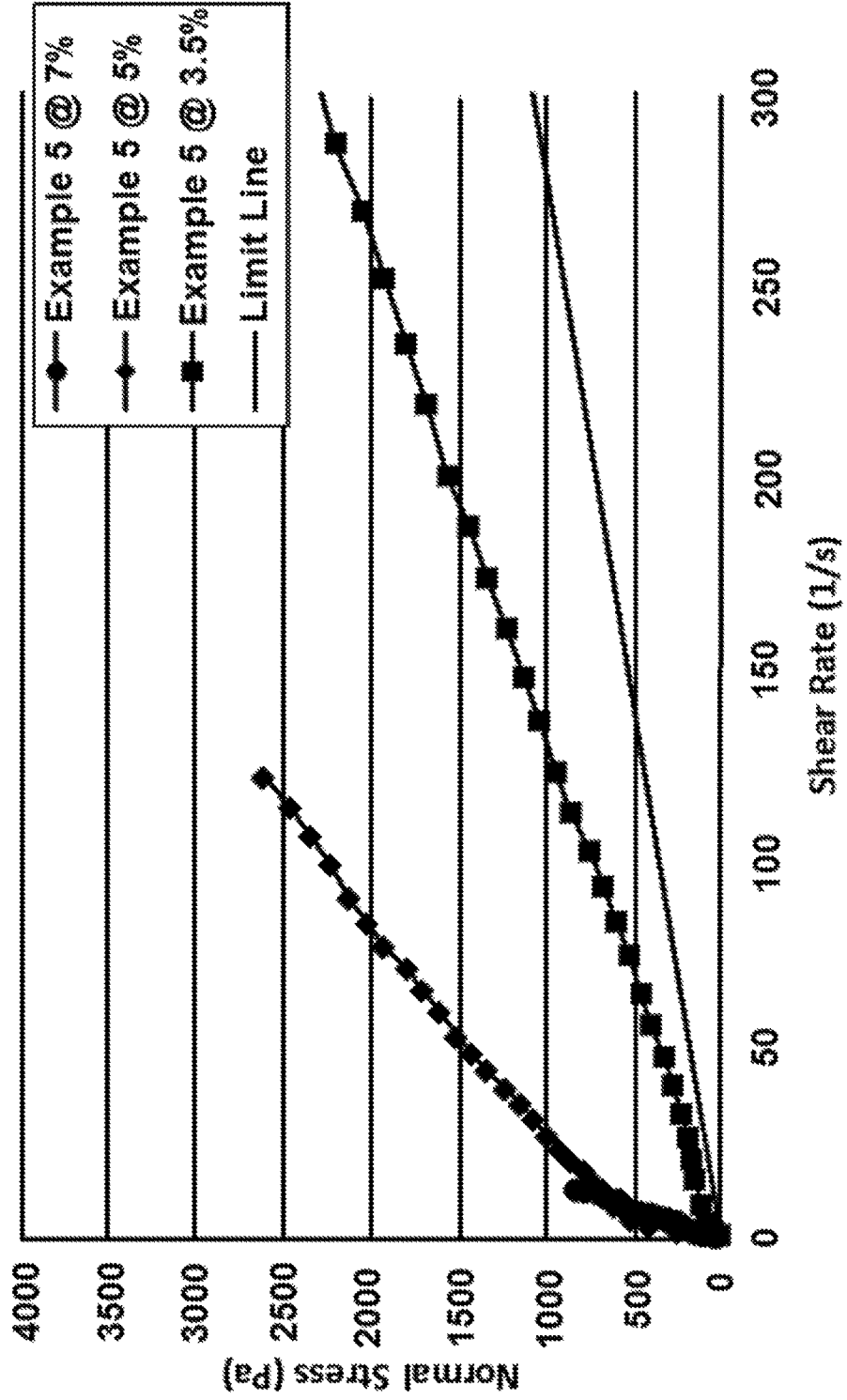
FIG. 9B is a line graph of stress as a function of shear of the pituitous silicone fluid of Example 5.

The diluted materials were measured on a TA Instruments AR 1000-N controlled force rheometer. FIG. 9 displays a plot of the Normal Stress (Pa) versus the Shear Rate (1/sec), along with Viscosity (Pa·s) versus Shear Rate (1/sec), for the pituitous silicone fluid dilutions described above. The concentrated (or firm) gel gained its pituitous rheology as it was diluted down to 7 wt %, and maintained a normal stress curve above the limit line at 5 wt % and 3.5 wt %, while also significantly reducing viscosity.

Example 6: Hydrosilylation Reaction Product—6.25 wt % in Carrier Fluid

Into a reaction flask, the following raw materials were loaded: 12.32 g of the 9,502DP vinyl terminated siloxanes described above, 0.149 g of the 100DP siloxane with 6 pendant SiH sites described above, 187.92 g of isododecane, and 0.078 g of the platinum catalyst solution described above (which is approximately 2.0 ppm of Pt relative to the total batch size). Agitation began and the reaction flask was heated to 75° C. After approximately 45 minutes of reaction time, stirring was stopped, as the reaction mixture had become increasingly viscous. The product was held static for an additional two hours at 75° C., and then the platinum catalyst was inhibited with 0.50 g of a 1% solution of triphenylphosphine in the 2 cSt polydimethylsiloxane.

Figure 10:
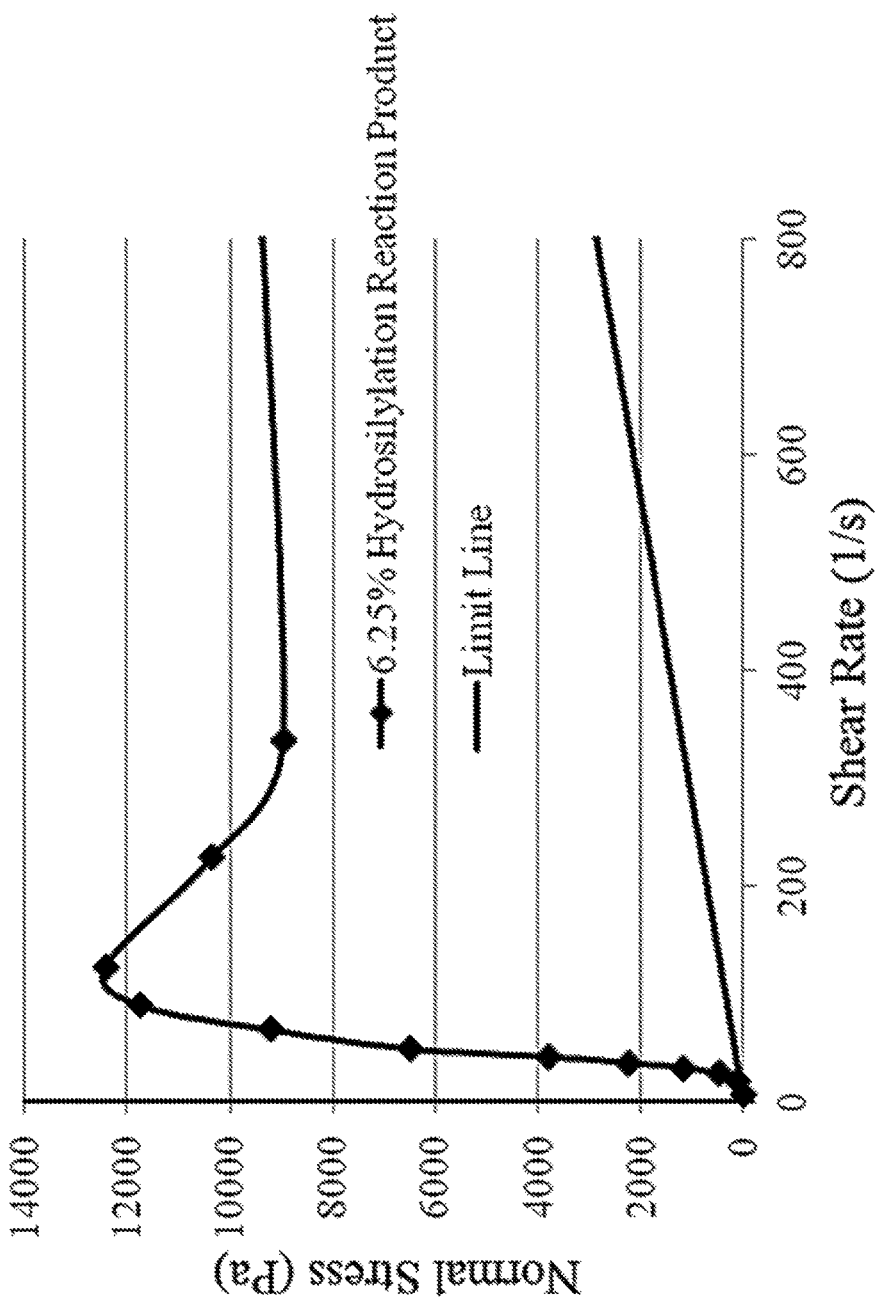
FIG. 10 is a line graph of stress as a function of shear of the pituitous silicone fluid of Example 6.

Once the reaction was complete, the product was allowed to cool to room temperature prior to characterization. FIG. 10 displays a plot of the Normal Stress (Pa) versus the Shear Rate (1/sec) for the pituitous silicone fluid described above.

Example 7: Hydrosilylation Reaction Product—6.25 wt % in Carrier Fluid

Into a reaction flask, the following raw materials were loaded: 18.64 g of the 9,502DP vinyl terminated siloxane described above, 0.24 g of a 100DP siloxane with 5 pendant SiH sites and a methyl-phenyl site with one equivalent of α-methyl styrene; 280.96 g of the 2 cSt polydimethylsiloxane, and 0.12 g of the platinum catalyst solution described above (which is approximately 2.0 ppm of Pt relative to the total batch size). Agitation began and reaction flask was heated to 75° C. After approximately 6 hours of reaction time, stirring was stopped, as the reaction mixture had become increasingly viscous. The product was held static for an additional two hours at 75° C.

Once the reaction was complete, the product was allowed to cool to room temperature prior to characterization. FIG. 11 displays a plot of the Normal Stress (Pa) versus the Shear Rate (1/sec) for the pituitous silicone fluid described above.

Example 8: 5% Oil in Water Emulsion

Phase A ingredients were added to a mixing vessel while mixing at 1,000 RPM with a marine propeller type blade. Phase B ingredients were added in a separate mixing vessel until homogeneous. Phase B ingredients were then added to phase A while mixing at 1,000 RPM. After 5 minutes, mixing was increased to 1,100 RPM for an additional 5 minutes. Mixing was then increased to 1,200 RPM for the remainder of the addition. After addition was complete, mixing was continued at 1,200 RPM for an additional 10 minutes to form a pituitous silicone fluid in the form of an emulsion. The average viscosity of this emulsion, reported as an average of the measured viscosity of 15 independent samples, is about 94,000± about 2,700, cps at 23° C.

| Ingredient | % wt |
|---|---|
| Phase A | |
| Hydrosilylation reaction product | 5.0 |
| Dimethicone | 25.0 |
| Sodium Polyacrylate (and) Dimethicone (and) Cyclopentasiloxane (and) Trideceth-6 (and) PEG/PPG-18/18 Dimethicone | 4.0 |
| Phase B | |
| Water | 63.0 |
| Glycerine | 3.0 |
| Preservative | 0.10 |

Example 9: 25% Oil in Water Emulsion

Phase A ingredients were added to a mixing vessel while mixing at 1,000 RPM with a marine propeller type blade. Phase B ingredients were added in a separate mixing vessel until homogeneous. Phase B ingredients were then added to phase A while mixing at 1,000 RPM. After 5 minutes, mixing was increased to 1,100 RPM for an additional 5 minutes. Mixing was then increased to 1,200 RPM for the remainder of the addition. After addition was complete, mixing was continued at 1,200 RPM for an additional 10 minutes to form a pituitous silicone fluid in the form of an emulsion. The average viscosity of this emulsion, reported as an average of the measured viscosity of 15 independent samples, is about 99,000± about 2,350, cps at 23° C.

| Ingredient | % wt |
|---|---|
| Phase A | |
| Hydrosilylation reaction product | 25.0 |
| Dimethicone | 5.0 |
| Sodium Polyacrylate (and) Dimethicone (and) Cyclopentasiloxane (and) Trideceth-6 (and) PEG/PPG-18/18 Dimethicone | 4.0 |
| Phase B | |
| Water | 63.0 |
| Glycerine | 3.0 |
| Preservative | 0.10 |

The data above evidences robust formulation capability and decreased sensitivity to raw material components and stoichiometry along with high quality of product formation and ease of processing with the particular raw materials utilized, as will be appreciated by those in the art, e.g. when compared with the existing art. Moreover, this disclosure utilizes fluids already having INCI names, which eliminated a need to secure a new INCI name.

One or more of the values described above may vary by ±5%, ±10%, ±15%, ±20%, ±25%, etc. so long as the variance remains within the scope of this disclosure. Unexpected results may be obtained from each member of a Markush group independent from all other members. Each member may be relied upon individually and/or in combination and provides adequate support for specific embodiments within the scope of the appended claims. The subject matter of all combinations of independent and dependent claims, both single and multiple dependent, is herein expressly contemplated. It is contemplated that any and all values or ranges of values between those described above may also be utilized. This disclosure is illustrative including words of description rather than of limitation. Many modifications and variations of the present disclosure are possible in light of the above teachings, and the disclosure may be practiced otherwise than as specifically described herein.

What is claimed is:

1. A pituitous silicone fluid comprising:
   (1) a hydrosilylation reaction product of;
      (a) a first linear organopolysiloxane comprising $(R^1R^2R^3SiO_{1/2})$ and $(R^4R^5SiO_{2/2})$ units, wherein each of $R^1$ to $R^5$ is independently a hydrocarbon group so long as at least one of $R^1$ to $R^5$ is an alkenyl group, said first linear organopolysiloxane comprises less than 1 weight percent of T and Q units, and said first linear organopolysiloxane has a degree of polymerization of from 100 to 15,000, and
      (b) a second linear organopolysiloxane comprising $(R^6R^7R^8SiO_{1/2})$ and $(R^9R^{10}SiO_{2/2})$ units, wherein each of $R^6$ to $R^{10}$ is independently is a hydrocarbon group, polyether group, siloxane group, or polyol group, so long as at least one of $R^6$ to $R^{10}$ is a hydrogen atom, said second linear organopolysiloxane comprises less than 1 weight percent of T and Q units, and said second linear organopolysiloxane has a degree of polymerization of from 4 to 1,000; and
   (2) a carrier fluid chosen from a silicone fluid, an organic solvent, an organic oil, and combinations thereof;
      wherein said hydrosilylation reaction product comprises alkenyl or Si-H functionality,
      wherein said hydrosilylation reaction product is present in an amount of from 3 to 30 parts by weight per 100 parts by weight of said pituitous silicone fluid,
      wherein the combination of said hydrosilylation reaction product and said carrier fluid provides said pituitous silicone fluid with a viscosity of from 0.1 to 75 Pa·s,
      wherein said pituitous silicone fluid exhibits an increasing normal stress observed in a perpendicular direction when a constantly increasing shear force is applied,
      wherein said pituitous silicone fluid is a liquid that can flow when a force is applied, and
      wherein fluids do not encompass gels, which do not flow.

2. The pituitous silicone fluid of claim 1, wherein said first linear organopolysiloxane is vinyl terminated.

3. The pituitous silicone fluid of claim 2, wherein said first linear organopolysiloxane is vinyl terminated, alternatively is dimethylvinyl terminated.

4. The pituitous silicone fluid of claim 1, wherein said second linear organopolysiloxane has 2 to 10 pendant Si-H sites.

5. The pituitous silicone fluid of claim 4, wherein said second linear organopolysiloxane has 6 pendant Si—H sites.

6. The pituitous silicone fluid of claim 1, wherein said second linear organopolysiloxane is dimethyl, methylhydrogen siloxane, trimethylsiloxy terminated.

7. The pituitous silicone fluid of claim 1, wherein:
   i) said hydrosilylation reaction product comprises vinyl functionality;
   ii) a molar ratio of vinyl to Si-H of said first and second linear organopolysiloxanes, respectively, is greater than 1; or
   iii) both i) and ii).

8. The pituitous silicone fluid of claim 1, wherein:
   i) said hydrosilylation reaction product comprises Si-H functionality;
   ii) a molar ratio of vinyl to Si-H of said first and second linear organopolysiloxanes, respectively, is less than 1; or
   iii) both i) and ii).

9. The pituitous silicone fluid of claim 1, wherein said carrier fluid is present in an amount of from 70 to 97 parts by weight per 100 parts by weight of said pituitous silicone fluid.

10. The pituitous silicone fluid of claim 1, wherein said carrier fluid is a silicone fluid.

11. The pituitous silicone fluid of claim 10, wherein said carrier fluid is a polydimethylsiloxane.

12. The pituitous silicone fluid of claim 1, wherein a plot of normal stress versus shear rate falls above a limit line on a graph and the limit line is created using the equation y=3.6x, where y is the normal stress and x is the shear rate.

13. The pituitous silicone fluid of claim 1, wherein said first linear organopolysiloxane has a degree of polymerization of from 2,000 to 15,000.

14. A personal care composition comprising a personal care additive and the pituitous silicone fluid of claim 1.

15. A personal care composition comprising a pituitous silicone fluid comprising:
   (1) the hydrosilylation reaction product of;
      (a) a first linear organopolysiloxane comprising $(R^1R^2R^3SiO_{1/2})$ and $(R^4R^5SiO_{2/2})$ units, wherein each of $R^1$ to $R^5$ is independently a hydrocarbon group so long as at least one of $R^1$ to $R^5$ is an alkenyl group, said first linear organopolysiloxane comprises less than 1 weight percent of T and Q units, and said first linear organopolysiloxane has a degree of polymerization of from 100 to 15,000, and
      (b) a second linear organopolysiloxane comprising $(R^6R^7R^8SiO_{1/2})$ and $(R^9R^{10}SiO_{2/2})$ units, wherein each of $R^6$ to $R^{10}$ is independently is a hydrocarbon group, polyether group, siloxane group, or polyol group, so long as at least one of $R^6$ to $R^{10}$ is a hydrogen atom, said second linear organopolysiloxane comprises less than 1 weight percent of T and Q units, and said second linear organopolysiloxane has a degree of polymerization of from 4 to 1,000; and
   (2) a carrier fluid chosen from a silicone fluid, an organic solvent, an organic oil, and combinations thereof;
      wherein said hydrosilylation reaction product comprises alkenyl or Si-H functionality,
      wherein said hydrosilylation reaction product is present in an amount of from 3 to 30 parts by weight per 100 parts by weight of said pituitous silicone fluid,
      wherein the combination of said hydrosilylation reaction product and said carrier fluid provides said pituitous silicone fluid with a viscosity of from 0.1 to 75 Pa·s, wherein said pituitous silicone fluid exhibits an increasing normal stress observed in a perpendicular direction when a constantly increasing shear force is applied, wherein said pituitous silicone fluid is a liquid that can flow when a force is applied, and wherein fluids do not encompass gels, which do not flow.

16. A method of forming a pituitous silicone fluid, said method comprising reacting a first linear organopolysiloxane and a second linear organopolysiloxane via a hydrosilylation reaction in the presence of a hydrosilylation catalyst and a carrier fluid to form a hydrosilylation reaction product comprising alkenyl or Si-H functionality;

wherein the first linear organopolysiloxane comprises $(R^1R^2R^3SiO_{1/2})$ and $(R^4R^5SiO_{2/2})$ units, wherein each of $R^1$ to $R^5$ is independently a hydrocarbon group so long as at least one of $R^1$ to $R^5$ is an alkenyl group, wherein the first linear organopolysiloxane comprises less than 1 weight percent of T and Q units, and wherein the first linear organopolysiloxane has a degree of polymerization of from 100 to 15,000;

wherein the second linear organopolysiloxane comprises $(R^6R^7R^8SiO_{1/2})$ and $(R^9R^{10}SiO_{2/2})$ units, wherein each of $R^6$ to $R^{10}$ is independently is a hydrocarbon group, polyether group, siloxane group, or polyol group, so long as at least one of $R^6$ to $R^{10}$ is a hydrogen atom, wherein the second linear organopolysiloxane comprises less than 1 weight percent of T and Q units, and wherein the second linear organopolysiloxane has a degree of polymerization of from 4 to 1,000;

wherein the carrier fluid is chosen from a silicone fluid, an organic solvent, an organic oil, and combinations thereof, wherein the hydrosilylation reaction product is present in an amount of from 3 to 30 parts by weight per 100 parts by weight of the pituitous silicone fluid, wherein the combination of said hydrosilylation reaction product and said carrier fluid provides said pituitous silicone fluid with a viscosity of from 0.1 to 75 Pa·s, wherein the pituitous silicone fluid exhibits an increasing normal stress observed in a perpendicular direction when a constantly increasing shear force is applied, wherein said pituitous silicone fluid is a liquid that can flow when a force is applied, and wherein fluids do not encompass gels, which do not flow.

17. The method of claim 16, wherein the second linear organopolysiloxane comprises the reaction product of a first species of the second linear organopolysiloxane and a compound having a mono terminal aliphatic unsaturated hydrocarbon group.

18. The method of claim 16, wherein
i) the first linear organopolysiloxane is vinyl terminated;
ii) the second linear organopolysiloxane has 2 to 10 pendant Si-H sites; or
iii) both i) and ii).

* * * * *